US007790865B1

(12) United States Patent
Heath et al.

(10) Patent No.: US 7,790,865 B1
(45) Date of Patent: Sep. 7, 2010

(54) ELUTING REAGENTS, METHODS AND KITS FOR ISOLATING DNA

(75) Inventors: Ellen M. Heath, Minnetonka, MN (US); Ruth M. Shuman, Minnetonka, MN (US)

(73) Assignee: Qiagen North American Holdings, Inc, Germantown, MD (US)

( * ) Notice: Subject to any disclaimer, the term of this patent is extended or adjusted under 35 U.S.C. 154(b) by 0 days.

(21) Appl. No.: 09/241,637

(22) Filed: Feb. 2, 1999

(51) Int. Cl.
*C07H 21/04* (2006.01)
*C12Q 1/68* (2006.01)

(52) U.S. Cl. .................... 536/23.1; 536/24.3; 435/6; 435/91.1; 435/91.2; 435/287.1

(58) Field of Classification Search ............... 435/91.1, 435/184, 219, 87, 259; 536/23.1, 127
See application file for complete search history.

(56) References Cited

U.S. PATENT DOCUMENTS

| | | | |
|---|---|---|---|
| 4,430,496 A | | 2/1984 | Abbott |
| 4,935,342 A | | 6/1990 | Seligson et al. |
| 5,057,426 A | | 10/1991 | Henco et al. |
| 5,151,345 A | | 9/1992 | Hasebe |
| 5,187,083 A | | 2/1993 | Mullis |
| 5,234,809 A | * | 8/1993 | Boom et al. ............... 435/91.2 |
| 5,234,824 A | | 8/1993 | Mullis |
| 5,286,644 A | | 2/1994 | Doersem et al. |
| 5,342,931 A | * | 8/1994 | Woodard et al. .......... 536/25.4 |
| 5,405,951 A | | 4/1995 | Woodard |
| 5,496,562 A | | 3/1996 | Burgoyne |
| 5,599,667 A | | 2/1997 | Arnold et al. |
| 5,652,141 A | | 7/1997 | Henco et al. |
| 5,750,346 A | | 5/1998 | Bridgham et al. |
| 5,756,126 A | | 5/1998 | Burgoyne |
| 5,770,365 A | | 6/1998 | Lane et al. |
| 5,804,684 A | | 9/1998 | Su |
| 5,807,527 A | | 9/1998 | Burgoyne |
| 5,939,259 A | | 8/1999 | Harvey et al. |
| 5,973,137 A | * | 10/1999 | Heath ....................... 536/25.4 |
| 6,037,465 A | * | 3/2000 | Hillebrand et al. ....... 536/25.42 |
| 6,054,039 A | | 4/2000 | Shieh |
| 6,093,695 A | | 7/2000 | Rupar et al. |
| 6,136,555 A | | 10/2000 | Jones |
| 6,383,393 B1 | | 5/2002 | Colpan et al. |
| 6,969,603 B2 | | 11/2005 | Hayashizaki et al. |
| 7,173,124 B2 | | 2/2007 | Deggerdal et al. |

FOREIGN PATENT DOCUMENTS

| | | |
|---|---|---|
| EP | 0389063 | 9/1990 |
| EP | 0 580 305 A | 1/1994 |
| EP | 0580305 | 1/1994 |
| EP | 819696 A2 | 1/1995 |
| WO | WO 90/03959 | 4/1990 |
| WO | WO 99/03959 | 4/1990 |
| WO | WO 92 07863 A | 5/1992 |
| WO | WO 9207863 | 5/1992 |
| WO | WO 95 02049 A | 1/1995 |
| WO | WO 9502049 | 1/1995 |
| WO | WO 96/18731 | 6/1996 |
| WO | WO 97/10331 | 8/1996 |
| WO | WO 98 03674 A | 1/1998 |
| WO | WO 9803674 | 1/1998 |
| WO | WO 98/51693 | * 11/1998 |
| WO | WO 99/13976 | 3/1999 |

OTHER PUBLICATIONS

Harding et al. Rapid isolation of DNA from complex biological samples using a novel capture reagent-methidium spermine-sepharose, Nucleic Acids Research, pp. 6947-6958, 1989.*
GIBCO-BRL, Concert-Rapid Plasmid Purification Systems. Life-technologies Catalog Series 11453, May 1998.*
Sambrook et al. Molecular Cloning: A Laboratory Manual. vol. 3, Appendix sections B.11 and B.20. (1989).*
Kaur et al. Selective recovery of DNA fragments from silica particles: effect of A-T content and elution conditions. 1995 Nucleic Acids Research vol. 23(23): pp. 4932-4933.*
de Nijs et al. Isolation of Fusarium DNA for molecular analysis with and without mechanical cell disruption. 1996 Journal of Microbiological Methods, vol. 27. pp. 13-17.*
van Huynh, et al. Anal Biochem 1993; 211:61-65.*
Reed, K.C., et al., "Rapid Preparation of DNA Dot Blots From Tissue Samples, Using Hot Alkaline Lysis and Filtration Onto Charge-modified Nylon Membrane" Nucleic Acids Research, 18 (10), pp. 3093 (1990).
McCabe, et al., "DNA Microextraction from Dried Blood Spots on Filter Paper Blotters: Potential Applications to Newborn Screening", Hum. Gent. 75(3): 213-216 (Mar. 1987).
Walsh, et al., "Chelex 100 as a Medium for Simple Extraction of DNA for PCR-Based Typing from Forensic Material", Bio Techniques, vol. 10, No. 4 pp. 506-513 (Apr. 1991).
Nordvag, et al. and El-Gewely, "Direct PCR of Washed Blood Cells", Bio Techniques, vol. 12, No. 4: pp. 490-492 (Apr. 1992).
Carducci, et al. "DNA Elution and Amplification by Polymerase Chain Reaction from Dried Blood Spots", Bio Techniques, vol. 13, No. 5: pp. 735-737 (Nov. 1992).
Berlin, et al. "Rapid Preparation of Genomic DNA Form Dried Blood and Saliva Spots for Polymerase Chain Reaction", Human Mutation, 1: pp. 260-261 (Jun. 1992).
Makowski, et al., Enchanced direct amplification of Guthrie card DNA following selective elution of PCR inhibitors, Nucl. Acids Research, vol. 23, No. 18 pp. 3788-3789 (1995).
Reed, K.C., et al., "Rapid Preparation of DNA Dot Blots from Tissue Samples, Using Hot Alkaline Lysis and Filtration onto Charge-modified Nylon Membrane" Nucleic Acids Research, 18 (10), p. 3093 (1990).
Deggerdal, et al., "Rapid Isolation of PCR-Ready DNA from Blood, Bone Marrow and Cultured Cells, Based on Paramagnetic Beads" Biotechniques, vol. 22, No. 3, pp. 554-557, (Mar. 1, 1997).
Dynal Catalog, Technical Handbook, 3$^{rd}$ Edition, p. 28 (1998).

(Continued)

Primary Examiner—Jeanine A Goldberg
(74) Attorney, Agent, or Firm—Baker Donelson Bearman, Caldwell & Berkowitz, PC

(57) ABSTRACT

Eluting reagents and methods for isolating DNA from biological materials are provided.

21 Claims, No Drawings

OTHER PUBLICATIONS

Harvey et al., "Impregnated 903 Blood Collection Paper: A Tool for DNA Preparation from dried Blood Spots for PCR Amplification." Clinical Chemistry. vol. 41, No. 6, p. S108, 1995.

Hawkins et al, "DNA Purification and Isolation Using a Solid-Phase", Nucleic Acids Research, 22, 4543-4544 (1994).

* cited by examiner

```
                        SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer sequence

<400> SEQUENCE: 1
gaaactggcc tccaaacact gccc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer sequence

<400> SEQUENCE: 2
gtcttgttgg agatgcacgt gccc                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:  Primer
      having sequence specific to the human betaglobin gene
      (sense strand).
```

```
<400> SEQUENCE: 3
cctggctcac ctggacaacc tcaa                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:  Primer
      with sequence specific to the human betaglobin gene
      (anti-sense strand).

<400> SEQUENCE: 4
tagccacacc agccaccact ttct                                              24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence :
<220> FEATURE:
<223> OTHER INFORMATION: Description of Artificial Sequence: Primer
      specific to a sequence of the HLA-H gene used for
      hereditary hemochromatosis genetic screening

<400> SEQUENCE: 5
tggcaagggt aaacagatcc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:  Primer
      specific to a region of the HLA-H gene used for
      hereditary hemochromatosis genetic screening.

<400> SEQUENCE: 6
ctcaggcact cctctcaacc                                                   20
```

ELUTING REAGENTS, METHODS AND KITS FOR ISOLATING DNA

BACKGROUND OF THE INVENTION

Nucleic acids such as DNA, are used extensively in the field of molecular biology for research and clinical analyses. Common methods for analyzing DNA are Southern blotting, amplification through methods such as polymerase chain reaction (PCR), and sequencing. Using these methods, differences in DNA sequence are determined to aid in gene identification, population screening, pathogen identification and diagnostic testing. All of these analyses require purified DNA samples as the basis for consistent and valid results.

There are numerous nucleic acid purification methods that fall into two general categories, liquid phase and solid phase purification. In liquid phase purification, the DNA remains in the liquid phase while impurities are removed by precipitation and/or centrifugation. In solid phase purification, the DNA is bound to a solid support while impurities are selectively eluted. Both purification strategies utilize conventional methods, which require many steps and often hazardous reagents, as well as more rapid methods, which require fewer steps and usually less hazardous reagents.

Using conventional liquid phase methods, DNA is most commonly isolated using density gradient centrifugation, organic solvent extraction, or salt precipitation. Protocols describing these purification methods are given in Sambrook et al., *Molecular Cloning: A Laboratory Manual*, 2nd ed., 7.19-7.25, 9.16-9.19, Cold Spring Harbor Press, Cold Spring Harbor, N.Y. (1989) and Ausubel, et al., *Current Protocols in Molecular Biology*, 4.4.2-4.4.4 (1987). Briefly stated, the liquid phase purification methods of density gradient centrifugation, phenol-chloroform extraction, and salt precipitation generally require four main steps: lysing the cells to release the DNA from cellular and nuclear membranes; removing impurities (such as proteins, lipids and carbohydrates); concentrating by alcohol precipitation; and then rehydrating the DNA in a hydration solution. The major differences among these three methods occur during the second step, where impurities are removed from the DNA by density differentiation, organic-aqueous phase partitioning, or selective salt precipitation.

A conventional liquid phase purification method for purifying blood dried on specimen collection cards (Guthrie cards) is described by McCabe et al., *Human Genetics*, 75, 213-216 (1987). The method follows closely a procedure for liquid blood described in Sambrook et al., *Molecular Cloning: A Laboratory Manual*, 2nd ed., 9.16-9.19, Cold Spring Harbor Press, Cold Spring Harbor, N.Y. (1989). In this phenol extraction method, dried white cells are removed from the collection paper by rehydrating with a saline solution. The white cells are incubated in a buffer to lyse the cells. Then, three phenol extractions are performed to remove protein impurities followed by three ether extractions to remove the phenol. The DNA is concentrated by sodium acetate-ethanol precipitation, washed with 70% ethanol and then rehydrated in a standard DNA hydration solution. Several reagents (ten), two of which are hazardous (phenol and ether), are typically required for this method. Although these conventional methods typically yield highly purified DNA preparations, they are laborious and hazardous.

As with liquid phase purification, conventional solid phase methods have been developed to generate highly purified DNA. Generally these methods require four general steps: lysing cells to release DNA from cellular and nuclear membranes; binding the released DNA to a solid support; washing away impurities; and then eluting the purified DNA. The first two steps, lysing the cells and binding the released DNA, usually require hazardous reagents at high concentration.

For solid phase DNA purification, many solid supports have been used including membrane filters, magnetic beads, metal oxides, and latex particles. Probably the most widely used solid supports are silica-based particles (see, e.g., U.S. Pat. No. 5,234,809 (Boom et al.); International Publication No. WO 95/01359 (Colpan et al.); U.S. Pat. No. 5,405,951 (Woodard); International Publication No. WO 95/02049 (Jones); WO 92/07863 (Qiagen GmbH). For example, the method disclosed in U.S. Pat. No. 5,234,809 (Boom et al.) uses a high concentration chaotropic solution to bind DNA to silica particles and requires six centrifugation steps and five reagents to purify DNA from whole blood. Disadvantages of this method are the use of a particulate suspension, the use of many centrifugation steps, and the use of hazardous reagents, such as guanidinium isothiocyanate and acetone.

One means for simplifying the conventional solid phase purification procedures is to eliminate the elution step and use the DNA while it is bound to a solid support for subsequent analyses, such as amplification. Thus, by using immobilized DNA, usually at least one reagent and one step is omitted. For example, U.S. Pat. No. 5,234,809 (Boom et al.) describes such a method for purifying DNA, although it is not present in a complex mixture such as blood. Using the method described above, but omitting the elution step, reduces the number of reagents and steps by one.

In another example, U.S. Pat. No. 5,496,562 (Burgoyne) describes a method of purifying cellulose filter paper containing dried blood that uses four reagents during four phenol washes and five isopropanol washes. After drying, a small piece of the filter paper is cut from the square and used directly as a substrate for PCR amplification. Despite the use of bound DNA for analysis, these methods still require many steps and hazardous reagents.

Recently, there has been a trend toward developing more rapid and simple methods for both liquid and solid phase purification. This has been driven in part by the development of DNA amplification assays which reduce the time necessary for analysis. As the number of DNA-based assays has increased in the field, there is a need for more rapid means of processing the biological samples. Also, using simpler methods reduces the risk of sample cross-contamination by reducing the number of sample handling steps. In addition, the simpler the method, the more readily the process may be automated.

One rapid liquid phase method for DNA purification uses a chelating resin to remove metal impurities from liquid blood or blood stains (Walsh et al., BioTechniques, 10, 506-513 (1991)). Using this method, blood cells are first washed with deionized water and then incubated with a suspension of the chelating resin and deionized water at 56° C. for 15-30 minutes. This incubation is followed by vortexing, incubating at 100° C. for 8 minutes, vortexing again, and removing the impurities by centrifugation. This method is rapid (completed in 45-75 minutes) and simple (requires only two reagents).

Another simple and rapid method for liquid phase DNA purification is described by Nordvag et al., *BioTechniques*, 12, 490-492 (1992). Starting with whole human blood, the blood cells are washed twice with a solution of 10 mM EDTA and 10 mM NaCl and collected by microcentrifugation after each wash. Then the cells are resuspended in 50 mM Tris (hydroxymethyl)aminomethanehydrochloric acid (Tris-HCl) buffer (pH 8.0) and boiled for 3 minutes prior to PCR amplification. For this purification method, only two reagents are required, both of which are generally nonhazardous. Furthermore, the method requires only approximately 15 minutes.

An even simpler single reagent method is described by Carducci et al., *BioTechniques*, 13, 735-737 (1992). Using this procedure, a 3 mm diameter blood spot is autoclaved for 3 minutes and then boiled for 5 minutes or sonicated for 10 minutes in a PCR-compatible buffer (10 mM Tris-HCl pH 8.3, 50 mM KCl, 3 mM $MgCl_2$ and 0.001 gelatin). The impurities remain bound to the disk following autoclaving while the DNA is recovered in the buffer.

All three of these liquid phase methods for DNA purification use low concentrations, nonhazardous reagents, and simplified methods. However, these three methods (Walsh et al., Nordvag et al., and Carducci, et al.) could be simplified further by eliminating the use of resins (which must be uniformly suspended prior to use), eliminating the repetitive washing of cells, or eliminating the cumbersome autoclaving of blood spots.

Rapid and simple methods for solid phase DNA purification have also been developed. The procedure of Berlin et al., *Human Mutation*, 1, 260-261 (1992) describes washing dried blood spots successively with a nonionic detergent-containing buffer. To elute the DNA from the filter paper, each sample is incubated at 65° C. for one hour with another nonionic detergent-containing buffer containing a proteinase K solution. A final incubation at greater than 95° C. for 10 minutes is necessary to inactivate the proteinase K. This method reduces the number of reagents required to three, but has the disadvantages of using an enzyme, a long incubation time, and a high incubation temperature (i.e., greater than 95° C.).

A rapid method using a membrane filter as a means of trapping DNA is disclosed in U.S. Pat. No. 5,234,824 (Mullis). Typically, this method requires a high concentration lysing reagent to lyse cells present in whole blood. Then, the lysate is applied to a filter and washed successively with a second lysing reagent and then either buffer or water to further purify the DNA. The DNA is eluted from the membrane by boiling for 15 minutes in water or in a buffered reagent containing magnesium chloride. Disadvantages of this solid phase purification method include the absence of a chelating agent in the purification and elution reagents, which can increase the probability of DNA damage (e.g., due to nucleases). In addition, there is a requirement for a cumbersome high temperature incubation (i.e., about 100° C.).

In another example, W.O. Pat. No. 96/18731 (Deggerdal) describes a method of purifying DNA from cells by mixing the cells with a detergent and a solid phase made up of magnetic beads. In this method, cells may be pre-lysed by the detergent to release the DNA which is subsequently bound to the solid phase. Alternatively, detergent may be added to a suspension made up of the cells and the solid phase, or the cells, detergent, and solid phase may be suspended together to allow the detergent to lyse the cells in the liquid phase and subsequently bind the DNA to the solid phase. However, this method involves multiple steps of adding or removing the liquid phase (i.e., detergent or the cell debris-detergent suspension) from the solid phase.

A very simple method is presented by Makowski et al., *Nucleic Acids Research*, 23, 3788-3789 (1995) in which 3 mm diameter disks punched from blood samples dried on cellulose collection paper are washed with deionized water (two 30 minute washes) and used directly for PCR amplification. As discussed in the above analysis of the '824 patent, a major disadvantage of using deionized water as a purification reagent is that the absence of a chelating agent increases the probability of DNA damage (e.g., due to nucleases). In addition, the absence of a detergent reduces the efficiency with which impurities are solubilized.

Nucleic Acids may be detected and quantitated by several means. Commonly, UV absorbance at a wavelength of 260 nm is used. A wavelength of 320 nm is used to determine background absorbance. Also, fluorimetry in the presence of Hoechst 33258 dye (e.g., Hoefer, DyNA Quant Fluorimeter, Pharmacia Biotech, Piscataway, N.J.), antibody detection strips (DNA Dipstick, Invitrogen, Carlsbad, Calif.), branched signal amplification (Chiron Corporation, Emeryville, Calif.), and quantitative PCR amplification (e.g., Applied Biosystems 7700, Perkin Elmer Applied Biosystems Division, Foster City, Calif.) are used to detect and quantitate nucleic acids.

As generally known and practiced, the purity of the DNA may be ascertained by measuring the absorbance at various wavelengths. The presence of impurities such as proteins, lipids, carbohydrates, cellular debris, etc. can increase the measured absorbance. In contrast, pure nucleic acids, especially DNA used in PCR amplification, have a substantially lower absorbance at established wavelengths.

Currently, there are numerous nucleic acid amplification systems available. While the most commonly used amplification methods are Polymerase Chain Reaction (PCR), other target amplification technologies include Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA).

PCR is used routinely to amplify one or more targeted nucleic acid sequences within a sample or mixture of nucleic acids. This process is disclosed in U.S. Pat. No. 4,965,188 (Mullis). For each target nucleic acid sequence to be amplified in this process, separate complementary strands of nucleic acid are treated with two primers selected to be substantially complementary to portions of the target nucleic acid within the two strands. A thermostable enzyme (a polymerase) is generally used to extend the primers to form complementary primer extension products. When these are separated into their complementary strands, they serve as templates to extend the complementary primer into the target nucleic acid sequence. When separated, these in turn act as templates for synthesis of additional nucleic acid sequences. The PCR amplification process involves a series of simple steps. These include temperature cycling to cause hybridization of primers and templates, polymerase mediated synthesis of the primer extension products, and separation and subsequent annealing of the strands of template strands and the synthesized target nucleic acid sequences. Thus, there is an exponential increase in the amount of targeted nucleic acid sequences synthesized. PCR amplification is a very sensitive process. Therefore, a very high purity of starting sample is necessary.

LCR is another diagnostic technique that is often utilized in conjunction with a primary PCR amplification. LCR employs a thermostable ligase and allows the discrimination of DNA sequences differing in only a single base pair. LCR depends on highly pure NA templates due to its sensitivity.

Purified nucleic acids can be further analyzed by Southern hybridization, or Southern blotting as it is more commonly known. Southern blotting is the capillary transfer of DNA fragments from gels to various types of filter paper. It allows the researcher to detect rare sequences in a complex population of restriction fragments and is useful in gene cloning, reverse genetics, and the analysis of restriction-fragment-length-polymorphisms (RFLP's) for human genetic disease diagnosis. Southern blotting involves the digestion of DNA with one or more restriction enzymes, followed by a size separation by electrophoresis on an agarose gel. The DNA is then denatured in situ and transferred from the gel to a membrane (e.g., nitrocellulose or nylon). The DNA attached to the membrane is then hybridized to radiolabelled DNA or RNA, and autoradiography is used to locate the positions of bands complementary to the probe. Southern blotting is highly sensitive. A sequence of 1000 base pairs (bp) that occurs only once in the mammalian genome (i.e., 1 part in 3 million) can be detected in an overnight exposure if 10 μg of genomic DNA is transferred to the filter and hybridized to a probe several hundred nucleotides in length.

To advance the field of DNA sample preparation there is a need for solid phase DNA purification strategies. There is also a need for reagents and methods that are adaptable to solid phase purification strategies are not only simple and rapid but general in scope to maximize adaptability for automation. There is a need for reagents that are of generally low concentration, stable at room temperature (i.e., 20-25° C.), less hazardous (i.e., less corrosive, flammable or toxic), nonparticulate to eliminate the need for mixing, and protective of DNA quality. There is also a need for methods with few steps that can be performed using a variety of biological starting materials, whether hydrated or dried, especially as applied to routine testing as found in clinical laboratories. The reagents must not inhibit subsequent DNA analysis procedures by interfering with the buffering capacity of PCR buffers, or cause degradation of polymerase, primers or oligonucleotides used in DNA amplification. There is also a need for methods with few steps that can be performed using a variety of biological starting materials, whether hydrated or dried, especially as applied to routine testing as found in clinical laboratories.

The reagents and methods used in the solid phase purification strategy must also not interfere with standard methods for nucleic acid quantification, restriction enzyme digestion, DNA sequencing, hybridization technologies, such as Southern Blotting, etc., and amplification methods such as Polymerase Chain Reaction (PCR), include Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), or other DNA analysis.

SUMMARY OF THE INVENTION

The present invention provides reagents, methods, and kits that incorporate a solid support for purifying, amplifying, and characterizing DNA from liquid and dried biological samples. The purified DNA is suitable for use in subsequent widely used techniques such as amplification and restriction enzyme digestion.

The reagents of the present invention generally contain low concentrations of buffers, salts, acids, bases, chelating agents, and/or detergents so that they are not significantly inhibitory to subsequent DNA analyses. In conventional systems, reagents containing high concentrations of one or more of these components are typically used for DNA purification. By using these low concentration reagents, the number of steps required for DNA purification is reduced making the method more rapid and simple. These reagents are also generally less hazardous than those used for conventional DNA purification. The solid phase purification methods described typically require only two main steps (e.g., washing and drying). If removal of DNA from a solid support (or solid support matrix) is required, another step (elution) is used.

A commercially available DNA purifying reagent is used in the present invention to solubilize and/or rupture cell or protein coat membranes facilitating the release of DNA and/or to solubilize impurities facilitating their removal. The composition of the DNA purifying reagent should render it compatible with (i.e., not significantly inhibitory to) subsequent DNA analyses, such as PCR amplification. For example, the molarity of the DNA purifying reagent should be low.

A DNA eluting reagent may be used to remove purified DNA from a solid support following solid phase purification. The DNA eluting reagent includes: a buffer to maintain the pH at least about 7 (preferably, at least about 8, more preferably, at least about 9, and most preferably, at least about 10); a base to adjust the reagent pH; a chelating agent; and deionized and substantially nuclease-free water. The buffer preferably has a pKa of at least about 8. A preferred buffer is Tris. The base is preferably one that can raise the pH of the reagent to no less than 7. The base is preferably an alkaline metal hydroxide. Such alkaline metal hydroxides include sodium hydroxide, potassium hydroxide, and lithium hydroxide. The chelating agent is preferably ethylenediamine-tetraacetatic acid (EDTA) or cyclohexanediamine-tetraacetatic acid (CDTA). However, any chelating agent capable of reducing nuclease activity is suitable for use. The combined amount of buffer, base, and chelating agent is of low concentration (typically, no greater than about 20 mM), rendering it generally compatible with (i.e., not significantly inhibitory to) subsequent DNA analyses, such as PCR amplification or restriction enzyme digestion.

Suitable solid supports include cellulose, cellulose acetate, glass fiber, nitrocellulose, nylon, polyester, polyethersulfone, polyolefin, polyvinylidene fluoride, and combinations thereof. A preferred solid support is composed of cellulose such as that used commonly for specimen collection.

Where tissues, cell membranes, cell walls or viral protein coats are resistant to lysis by desiccation or treatment with a DNA purifying reagent containing a non-ionic detergent, the solid support may be treated with a lysing reagent to assist in lysis and subsequent purification. In conventional methods, this lysing step is performed typically prior to contacting the biological material with the solid support. However, by adding a lysing reagent to the solid support, a step is eliminated and the method is simplified. Preferably, the lysing reagent is applied to the solid support and then dried on the solid support before contacting the biological material with the treated solid support, although this is not a necessary requirement.

The lysing reagent is used preferably for the purification of DNA and can be composed of an amount of a detergent effective to lyse cells or protein coats sufficiently to release DNA; a chelating agent to reduce DNA damage; water; and optionally, a buffer effective to provide a pH of greater than about 2. The detergent is preferably anionic. Examples of anionic detergents include N-lauroyl sarcosine or a dodecylsulfate salt. Sodium dodecylsulfate is a particularly preferred anionic detergent. The buffer is preferably effective to provide a pH of greater than about 6. Tris is a particularly preferred buffer. The chelating agent is preferably EDTA or CDTA.

Optionally, the lysing reagent can include an RNA digesting enzyme, such as RNase A, for the purpose of degrading RNA present in the biological sample. Including an RNA digesting enzyme eliminates the need for a separate RNase digestion step, as is typically required in conventional methods.

This invention also provides methods for purifying DNA from biological samples. The biological samples include, for example, cell or virus suspensions, body fluids, whole blood, bone marrow, buffy coat, plasma, cultured cells, all suspensions (e.g., bacteria, tissue homogenates) and environmental samples. The environmental samples include, for example, air, water or soil. For solid phase purification, the methods of the present invention involve contacting the biological sample with a solid support. A DNA purifying reagent is added to the solid support containing the biological sample to facilitate solubilization of impurities, lysis of cell walls, release of DNA from the cells and DNA binding to the solid support. Washing of the solid support with a DNA purifying reagent (preferably, at least twice) causes impurities to be removed from the solid support. The solid support containing the bound and purified DNA may be used directly in amplification or other analyses. Alternatively, the DNA may be removed using the DNA eluting reagent. To elute DNA from the solid support, the DNA eluting reagent is contacted with the solid support, incubated, and then removed.

Another aspect of this invention involves the combination of a DNA purifying reagent and/or the DNA eluting reagent with one or more optional ancillary reagents. The first ancillary reagent, an RBC lysis reagent, is used to lyse red blood cells and facilitate subsequent purification of NAs from the white blood cells contained in mammalian whole blood. The second and third ancillary reagents, a cell suspension reagent and lytic enzyme reagent, are used together to digest cell walls in yeast and Gram-positive bacteria prior to DNA purification. The fourth ancillary reagent, a protein digesting reagent is used to digest contaminating proteins. A fifth ancillary reagent, an isotonic solution is used to suspend DNA and/or cells as needed.

A further embodiment of the present invention is a method for purifying DNA from yeast and Gram-positive bacteria. The method involves combining the biological sample with a cell suspension reagent. The cell suspension reagent includes a buffer, a chelating agent, and a cell suspending agent to form a cell suspension. To the cell suspension is added a lytic enzyme reagent. The lytic enzyme reagent includes an enzyme to digest cell walls, a buffer, an acid to adjust the pH of the reagent, and two stabilizing agents. The digested cells may be used for liquid or solid phase purification described above.

The present invention also provides kits for purifying DNA comprising instruction means for preparing substantially pure DNA from a biological sample and one or all of the following: a DNA purifying reagent, a DNA eluting reagent, a lysing reagent, an RBC lysis reagent, a cell suspension reagent, a lytic enzyme reagent, an isotonic solution or any combination thereof. The kit can also include a solid support, either untreated or treated treated with a lysing reagent. In addition, the kit can include a vessel to contain the solid support. Substantially pure nucleic acids are those that are suitable for use in subsequent analyses known to those with skill in the art, for example, DNA amplification, reverse transcription, and restriction enzyme digestion.

DETAILED DESCRIPTION OF THE INVENTION

The present invention provides reagents, methods and kits for incorporating a solid support purifying, amplifying, and characterizing DNA from biological samples. Such biological samples include biological material, typically in an aqueous mixture or dried, that contains nucleic acids (NAs) like DNA, including complex biological mixtures of prokaryotic or eukaryotic cells. Typically, the biological material also contains carbohydrates, proteins, and lipids. Biological materials include the following: body fluids such as whole blood, bone marrow, blood spots, blood serum, blood plasma, buffy coat preparations, saliva and cerebrospinal fluid, buccal swabs, cultured cells, cell suspensions of bacteria or tissue homogenates, solid animal tissues such as heart, liver and brain, body waste products, such as feces and urine, environmental samples taken from air, water, sediment or soil, plant tissues, yeasts, bacteria, viruses, mycoplasmas, fungi, protozoa, rickettsia, and other small microbial cells. Lysates or homogenates of these biological materials may also be used.

Preferably, the reagents, methods and kits incorporating a solid support of the present invention provide substantially pure DNA in any form. The DNA may be composed of, for example, chromosomal or genomic DNA, extrachromosomal DNA (such as mitochondrial and plasmid DNA), single stranded DNA, and viral DNA.

Using these reagents, methods, and kits incorporating a solid support, DNA of substantially high purity can be obtained. The purity of the DNA is determined by the substantial reduction of impurities, such as proteins, that could interfere with subsequent analyses, such as the sensitive RT-PCR and/or PCR assays. As used herein, "pure" means substantially free of carbohydrate, protein, and lipid impurities, such that the purified DNA can be used in subsequent analyses known to those with skill in the art. Thus, the isolated and purified DNA obtained according to the present invention is suitable for use in subsequent analyses. Preferably, the methods and kits of the present invention purify a wide range of DNA, all of which can be recovered over a wide molecular weight range.

This invention describes methods for using a low concentration reagent for purification of DNA. These methods are generally more rapid and simple than those used typically for DNA purification. The purified DNA obtained from these purification steps can be evaluated for purity, yield, size, amplification ability, etc.

The biological samples include, for example, cell or virus suspensions, body fluids, and tissue homogenates. If the biological sample consists of cells or viruses, the cells or viruses may be enumerated prior to this step. The enumeration may be conducted using standard cell counting methods such as an electronic cell counter (e.g., CBC5 Coulter Counter, Coulter Corp., Hialeah, Fla.) or a visual counter (e.g., a hemacytometer, Bright Line, American Optical, Buffalo, N.Y.).

The process for solid phase DNA purification consists of applying a biological sample to a solid support which may be treated with a lysing reagent. Contact with the solid support causes the cell and nuclear membranes to solubilize and/or rupture, thereby releasing the DNA which then binds to the solid support. The solid support may be heated to facilitate solubilization and rupture of the cell and nuclear membranes. The released DNA binds to the solid support allowing impurities to be removed by the addition of a first reagent. This first reagent may be a commercially available purifying reagent for DNA. Impurities are solubilized in the first reagent and are removed by suitable means such as centrifugation, pipetting, pressure, or vacuum leaving DNA is left bound to the solid support. Thus, the process uses only one reagent and two main steps (i.e., washing and the removal of excess aqueous solution). If DNA is removed from the solid support, an additional reagent, a DNA eluting reagent, is added and another step (eluting) is carried out.

For solid phase DNA purification, it may be necessary to remove the purified DNA from the solid support prior to analysis. The present invention also includes a low concentration DNA elution reagent for eluting DNA from a solid support. The composition of the low concentration DNA elution reagent may vary, but the total concentration is typically less than 20 mM for all compositions.

The low concentration DNA elution reagent, herein referred to as the "DNA Eluting Reagent," is capable of removing DNA from a solid support. It contains a base, a buffer, a chelating agent, and water in combination to maintain a pH of at least about 7, preferably, at least about 8, more preferably, at least about 9, and most preferably, at least about 10.

The DNA Eluting Reagent contains a buffer to maintain the pH at least about 7 and preferably has a pKa of at least about 8. Suitable buffers include, but are not limited to, N,N-bis[2-hydroxyethyl]glycine (available under the trade designation "BICINE" from Sigma Chemical Company, St. Louis, Mo.), 3-[cyclohexylamino]-2-hydroxy-1-propanesulfonic acid (available under the trade designation "CAPSO" from Sigma Chemical Company), and Tris. The buffer is used in an amount that is not significantly inhibitory to subsequent DNA analyses, such as PCR amplification. Thus, it is typically used in an amount of no greater than about 20 mM. Preferably, the buffer is Tris and is used in an amount of about 0.001-20 mM, more preferably, about 0.01-15 mM and most preferably, about 1-10 mM, based on the total volume of the reagent.

In addition to the buffer, the DNA Eluting Reagent contains a base to adjust the reagent pH. The base is used in an amount that is not significantly inhibitory to subsequent DNA analyses, such as PCR amplification. Thus, the base is typically used in an amount of no greater than about 20 mM. Such bases include, but are not limited to, potassium hydroxide and sodium hydroxide. Preferably, the base is an alkaline metal hydroxide like sodium hydroxide, potassium hydroxide, or lithium hydroxide and is used in an amount of about 0.2-20 mM, more preferably, about 0.5-15 mM, and most preferably, about 1-5 mM, based on the total volume of the reagent.

In addition to a buffer and a base, the DNA Eluting Reagent includes a chelating agent. A chelating agent is used in an amount effective to reduce DNA damage (e.g., by nuclease activity) during and following removal from the solid support so that the DNA is suitable for subsequent analyses. Suitable chelating agents are those capable of chelating divalent cations in aqueous media. Such chelating agents include, but are not limited to, ethylene diamine tetraacetate (EDTA) and cyclohexane diamine tetraacetate (CDTA). Preferably, the chelating agent is EDTA. In addition, the chelating agent is used in an amount that is not significantly inhibitory to subsequent DNA analyses, such as PCR amplification. Thus, it is typically used in an amount of no greater than about 0.1 mM. Preferably, the chelating agent is used in an amount of about 0.0001-0.1 mM, more preferably, about 0.005-0.05 mM, and most preferably, about 0.0015-0.015 mM, based on the total volume of the reagent.

The buffer, base and chelating agent are combined with water to form the DNA Eluting Reagent. The water is preferably deionized and nuclease free. The combined amount of buffer, base, and chelating agent is of low concentration (typically, no greater than about 20 mM), rendering it generally compatible with (i.e., not significantly inhibitory to) subsequent DNA analyses, such as PCR amplification or restriction enzyme digestion.

All the reagents used in purifying DNA from the source biological material have been formulated to be compatible with amplification and other analyses. The reagents have low concentrations of buffer, salt, detergent, and chelating agents that make them compatible with amplification analyses. The final purified nucleic acids are suspended in the DNA Eluting Reagent for solid phase nucleic acid extractions. Therefore, these reagents have been optimized for use in downstream DNA analyses. Such DNA analyses might include, but are not limited to, RT-PCR and PCR.

Currently available PCR amplification reactions from 3 manufacturers, Perkin Elmer, Promega, and Roche Molecular Biochemicals, are conducted in a 1× buffered solution that typically has the concentrations of Tris buffer, salt, and nonionic detergent at a basic pH between 8-10 as shown in Table 1.

TABLE 1

|  | PERKIN ELMER | PROMEGA | ROCHE MOLECULAR BIOCHEMICALS |
|---|---|---|---|
| Tris (mM) | 10 | 10 | 10 |
| KCl (mM) | 50 | 50 | 50 |
| Triton X-100 (%) | — | 0.1 | — |
| Gelatin (%) | 0.001 | — | — |
| $MgCl_2$ (mM) | ~1.5 | ~1.5 | ~1.5 |
| pH | 8.3 | 9.0 | 8.3 |

The lysing reagents and eluting reagents have Tris buffer concentrations that are either of the same order of magnitude or significantly lower than the concentrations found in PCR systems. Concentrations of Tris buffer in the eluting reagent typically range from 1-10 mM and will not inhibit or significantly interfere with the amplification process.

Another aspect of this invention involves the combination of the DNA purifying reagent and/or the DNA Eluting Reagent with one or more optional ancillary reagents. These ancillary reagents include reagents known to one of skill in the art for nucleic acid purification. The methods and kits of the present invention, however, are not limited to the use of these specific ancillary reagents, as one of skill in the art may use other reagents and/or techniques to achieve the same purpose. Also, the DNA purifying reagent and/or the DNA Eluting Reagent can be used with other reagents and/or techniques if desired.

The first ancillary reagent is a red blood cell lysing reagent used to lyse red blood cells and facilitate subsequent purification of DNA from the white blood cells contained in mammalian whole blood. This reagent is referred to herein as the "RBC Lysis Reagent" and contains ammonium chloride, sodium bicarbonate, and EDTA. Preferably, the ammonium chloride is used in the RBC Lysis Reagent at a concentration of about 140-150 mM, and more preferably, about 142-146 mM, based on the total volume of the reagent. Preferably, the sodium bicarbonate is used at a concentration of about 0.5-5 mM, and more preferably, about 0.5-2 mM, based on the total volume of the reagent. Preferably, the EDTA is used at a concentration of about 0.5-10 mM, and more preferably, about 0.75-1.25, based on the total volume of the reagent. RBC Lysis Reagent contains water, preferably of the purity described above. RBC Lysis Reagent is contacted with mammalian whole blood in an amount of 3 volumes of RBC Lysis Reagent to 1 volume of blood. The sample incubates about 1-30 minutes, preferably about 10 minutes, and white cells are separated from the sample by centrifuging at 15,000 for 20 seconds. All but about 1-3% of the supernatant fraction is discarded leaving the white cells available for DNA purification.

When combined with mammalian whole blood, the RBC Lysis Reagent forms a red cell lysate containing substantially intact white blood cells. It can also contain viruses with substantially intact protein coats. The white blood cells (and any cell-associated viruses that may be present) are then separated from the red cell lysate. The white blood cells can be combined with a nucleic acid purifying reagent directly or following application to a solid support.

The second and third ancillary reagents are used together to digest cell walls from yeast and Gram-positive bacteria prior to DNA purification. The reagents are referred to herein as "Cell Suspension Reagent" and "Lytic Enzyme Reagent." They are used in the first steps of the DNA purification procedure to digest cell walls that may be resistant to lysis by a nucleic acid purifying reagent. The Cell Suspension Reagent is combined with a biological sample to form a cell suspension. The Lytic Enzyme Reagent is combined with the cell suspension to form a mixture containing digested cells. These digested cells are then separated from the mixture by centrifugation, for example, and then contacted with the nucleic acid purifying reagent directly or following application to a solid support.

The Cell Suspension Reagent keeps cells intact while their cell walls are being digested by lytic enzymes. This reagent contains a buffer, preferably Tris, to maintain the reagent pH at about 7-8.5, and more preferably, about 7.5-8.0. The buffer is used preferably at a concentration of about 0.05-0.15 M, and more preferably, about 0.08-0.12 M, based on the total volume of the reagent. The Cell Suspension Reagent also contains a chelating agent, preferably EDTA, to reduce DNA damage. The chelating agent is used, preferably at a concentration of about 0.05-0.15 M, and more preferably, at about 0.08-0.12 M, based on the total volume of the reagent. The preferred molar ratio of buffer to chelating agent is about 1:1. This reagent also contains agents such as sorbitol, to keep cells intact while their cell walls are being digested. This agent is used preferably at a concentration of about 0.8-1.0 M, and more preferably, about 0.85-0.95 M, based on the total volume of the reagent. The buffer, chelating agent and cell suspending agent are combined with water. The water is preferably deionized and substantially nuclease-free.

The Lytic Enzyme Reagent contains a lytic enzyme that digests beta-1,3-glucose polymers that are contained in yeast cell walls. A purified form of this enzyme is readily available from commercial sources, such as Sigma Chemical Company, St. Louis, Mo. The activity of this enzyme is preferably at least about 200 units per mg, more preferably, at least about 1000 units per mg, and most preferably, at least about 5,000 units per mg. In addition to the enzyme, the Lytic Enzyme Reagent contains a buffer, preferably Tris, to maintain the reagent pH. Tris is used preferably at a concentration of about 1-20 mM, more preferably, about 5-15 mM, and most preferably, about 8-12 mM, based on the total volume of the reagent. The pH of the lytic enzyme reagent is adjusted to a pH of about 7.5-8.2 using an acid, such as hydrochloric acid. In addition, the Lytic Enzyme Reagent contains two stabilizing agents. The first is preferably glycerol. Glycerol is used preferably in an amount of about 20-50% glycerol (volume/volume), more preferably, about 24-40% glycerol, and most preferably, about 28-32% glycerol. The second stabilizing agent is preferably calcium chloride. Calcium chloride is used preferably at a concentration of about 0.5-5 mM, and more preferably, at about 0.75-1.25 mM, based on the total volume of the reagent. The enzyme, buffer, acid, and two stabilizing agents are combined with water. The water is preferably d.I. water. Preferably, the reagent is purified by passing through a filter of about 0.2 µM pore size.

Typically, to digest cell walls of yeast, for example, with the second and third ancillary reagents, 300 µl Cell Suspension Reagent are added to a 10-20 µl suspension of about 100 million yeast cells along with 1.5 µl Lytic Enzyme Reagent and incubated at 37° C. for 30 minutes. After centrifuging at 15,000×g for 1 minute, the supernatant fraction is removed leaving the digested cells available for DNA purification.

A fourth ancillary reagent, the protein digesting reagent, herein referred to as the "Protein Digesting Reagent," is used to digest contaminating protein, especially in solid tissue samples. A purified form of this enzyme, Proteinase K, is readily available from commercial sources such as Sigma Chemical Company and is used at a concentration of about 0.1 mg/mL. Heating at greater than 36° C. accelerates the activity of this enzyme.

A fifth ancillary reagent, an Isotonic Solution, is typically used to make cell or DNA suspensions. Suitable isotonic solutions are salt-based, often buffered with tris, citrate or phosphate. An example is phosphate buffered saline (PBS).

For solid phase purification, suitable solid supports include, but are not limited to, cellulose, cellulose acetate, glass fiber, nitrocellulose, nylon, polyethersulfone, polyester, polyolefin, polyvinylidene fluoride, and combinations thereof. A preferable solid support is composed of cellulose fibers such as found in the specimen collection paper 903 available from Schleicher and Schuell (Keene, N.H.) or BFC 180 available from Whatman International Ltd. (Springfield Mill, Kent, England). Another preferable solid support is polyolefin. Polyolefin is herein defined as any olefin based copolymer or homopolymer including modified polymers such as graft copolymers. Acceptable polyolefins include low, medium, and high density polyolefins and linear, low density polyethylene, polypropylene and polybutylene. Preferably, the polyolefin solid support is hydrophilic and composed of a mixture of low density polyethylene and polypropylene fibers such as those found in the Filtrona® polyolefin available from American Filtrona, Inc. (Richmond, Va.). Most preferably, the solid support is directionally porous giving uniform flow characteristics and low back pressure, is composed of fibers that are interlaced and bonded to each other, is resilient to allow for easy packing into a spin tube, well, cartridge, or another vessel, has a void volume of about 50-90% and is composed of fibers having a diameter of about 20-30 µm.

The size of the solid support suitable for use with the reagents of this invention may vary according to the volume of biological material. For example, when Schleicher and Schuell 903 paper, which has a thickness of 0.5 mm, is used for the solid support, a 3 mm diameter disk will hold about 3 µl blood and an 8 mm diameter disk will hold about 25 µl blood. As the volume of the biological material increases, the thickness and/or diameter may increase accordingly.

The shape of the solid support suitable for use with the reagents of this invention may vary according to the type of biological material. For example, when buccal, nasopharyngeal, vaginal, urethral, and rectal samples are obtained, a swab is an appropriate collection device. When body fluids such as blood or saliva samples are obtained, the solid support may be, for example, a sheet, a precut disk or a cylinder. If necessary, the solid support is contained in an appropriate vessel, e.g., a paper form (such as a Guthrie card), a microcentrifuge tube, a spin tube, a 96-well plate, a chamber, or a cartridge.

The solid support may be treated with a lysing reagent to assist in lysis and subsequent purification. Preferably, the volume of the lysing reagent used to treat the solid support is at least one-tenth of the total volume of the solid support. More preferably, the volume of the lysing reagent is at least half the total volume of the solid support, and most preferably, the volume of the lysing reagent corresponds to the total volume of the solid support. The total volume of the solid support refers to the volume defined by the external boundaries of the solid support. The resulting product is a lysing matrix for isolation of nucleic acids such as DNA, herein referred to as the "Lysing Matrix." By combining a lysing reagent with a solid support, the DNA purification method is simplified by removing a separate lysing step. Preferably, the lysing reagent is applied to the solid support and then dried on the solid support before contact with the biological material. In contrast, conventional systems typically contact the biological material with the lysing reagent as a step prior to contact with the solid support, or the biological material is suspended with the solid support after which the lysis reagent is added to the resulting suspension.

Optionally, the lysing reagent can include an RNA digesting enzyme if it is necessary to digest RNA present in a biological sample. By combining an RNA digesting enzyme with a solid support, the DNA purification method is simplified by removing a separate digestion step. A preferred RNA digesting enzyme is RNase A. A purified form of this enzyme is readily available from commercial sources such as Sigma Chemical Company, St. Louis, Mo. Preferably, RNase A is added to the Lysing Reagent in an amount of about 0.005-1 mg per ml and more preferably, about 0.01-0.1 mg per ml. The activity of this enzyme is preferably at least about 50 units per mg and more preferably, at least about 100 units per mg.

In a preferred embodiment, the lysing reagent includes the anionic detergent and the RNA digesting enzyme, but does not include a chelating agent or a buffer. Suitable anionic detergents are capable of lysing cells and/or solubilizing proteins and lipids. Such anionic detergents include, but are not limited to, salts (e.g., sodium, potassium, lithium salts) of dodecyl sulfate as well as N-lauroyl sarcosine or a dodecyl-sulfate salt. Preferably, the anionic detergent is a dodecyl sulfate salt. Preferably, it is used in an amount of about 0.1-10%, more preferably, 0.2-1.6%, and most preferably, about 1.0-1.2% weight/volume, based on the total volume of the reagent. For biological samples with a high RNA content, such as cell culture suspensions, an RNA digesting enzyme is necessary. A preferred RNA digesting enzyme is RNase A. For biological samples with a high RNA content, commercially available RNase A, (e.g., Puregene® RNase A available at a concentration of 4 mg/mL, Gentra Systems Inc., Minneapolis, Minn.) is added to the anionic detergent solution in an amount of about 0.005-1 mg per mL and more preferably, about 0.01-0.1 mg per mL. The activity of this enzyme is preferably at least about 50 units per mg and more preferably, at least about 100 units per mg.

In yet another preferred embodiment, the lysing reagent includes only the anionic detergent, but does not include a chelating agent, buffer, or the RNA digesting enzyme. Anionic detergents are used as described above.

This invention also provides methods for purifying DNA from biological samples. For solid phase purification, the methods of the present invention typically use only one reagent and two main steps (e.g., washing and drying). The method involves contacting the biological sample with a solid support to lyse the cells thereby releasing the DNA which then binds to the solid support. A commercially available DNA purifying reagent is added to the solid support to facilitate solubilization and removal of impurities. Sequential washing of the solid support with this reagent causes impurities to be removed from the solid support. Prior to use in subsequent analysis, excess aqueous solution may be removed from the solid support containing the purified DNA by methods such as evaporation or centrifugation as described in examples 1, 2, and 3.

As an alternative to using the solid support containing the purified DNA in subsequent analyses, the DNA may be removed from the solid support. An additional reagent and an additional step (eluting) are used if the DNA is removed from the solid support. Preferable, the DNA Eluting Reagent is used to remove DNA from the solid support. This is illustrated in Examples 4, 5, 7, 8, 9, 10, 11, and 13.

Preferably, the method involves contacting the solid support containing the DNA with the DNA Eluting Reagent and incubating. Preferably, the amount of DNA Eluting Reagent is about 0.25 volumes DNA Eluting Reagent to about 1 volume solid support, more preferably, the volume is about 1 volume reagent to about 1 volume solid support, and most preferably, the volume is about 4 volumes reagent to about 1 volume solid support.

The temperature of the incubation is, preferably, at least about 30° C., more preferably, at least about 80° C., and most preferably, at least about 100° C. The duration of the incubation is preferably, at least about 2 minutes, more preferably, at least about 5 minutes and most preferably, at least about 10 minutes. The DNA is removed from the solid support by standard methods, such as centrifugation, vacuum or pressure.

In a preferred embodiment, the solid support is treated with the Lysing Reagent such that the Lysing Reagent is bound to the solid support. The Lysing Reagent may be bound covalently, non-covalently, by being trapped within the interstitial spaces of the solid support, or by being deposited on the material (e.g., fibers, beads, etc.) of the solid support. The resulting product is a Lysing Matrix. Preferably, the Lysing Reagent is allowed to dry on the solid support.

The Lysing Reagent is added to the solid support, preferably at a volume corresponding to at least one-tenth of the total volume of the solid support, more preferably at a volume corresponding to at least half of the total volume of the solid support, and most preferably at a volume corresponding to at least the total volume of the solid support.

In another embodiment of the invention, the Lysing Reagent may be added directly to the material (e.g., fibers, beads, etc.) used in making the solid support and preferably allowed to dry before it is made into the final user-ready form (e.g., paper, swab, disk, plug, column, etc.). In yet another embodiment, the solid support may be treated with a crystalline or powder form of the lysing reagent and allowed to bind to the solid support.

DNA is isolated by allowing the sample of biological material (cultured cells, whole blood, etc.) to contact the Lysing Matrix. Although the sample may be treated with a lysing reagent before contact with the Lysing Matrix, the efficiency of purification and the DNA yield are greatly improved when the biological material is not pre-lysed. Thus, preferably, the biological material is added directly to the Lysing Matrix which lyses the cells and solubilizes protein coats and lipids. The efficiency of lysis may be improved by heating at greater than at least 30° C., more preferably at greater than at least 50° C., and most preferably at greater than at least 80° C. After at least 1 minute of incubating the sample within the Lysing Matrix, it is washed with the DNA purifying reagent. Sequential washing of the Lysing Matrix with the DNA purifying reagent causes impurities to be removed from the Lysing Matrix. Preferably, the amount of DNA purifying reagent used for DNA purification is about 0.5 volume DNA purifying reagent to about 1 volume of biological material, more preferably, about 2 volumes of DNA purifying reagent to about 1 volume of biological material, and most preferably, about 5 volumes of DNA purifying reagent to about 1 volume of biological material. Preferably, the number of washes with the DNA purifying reagent is at least two and more preferably, at least 3. This method is illustrated in Examples 7, 8, 9, 10, 12, and 13.

A further embodiment of the present invention is a method for purifying nucleic acids, like DNA, from yeast and Gram-positive bacteria. These biological materials are typically more resistant to lysis. The method involves combining the biological sample with a first ancillary reagent, i.e., a Cell Suspension Reagent (e.g., Cell Suspension Solution, Gentra Systems, Inc., Minneapolis, Minn.). The Cell Suspension Reagent includes a buffer, a chelating agent and a cell suspending agent to form a cell suspension. To the cell suspension is added a second ancillary reagent, i.e., a Lytic Enzyme Reagent (e.g., Lytic Enzyme Solution, Gentra Systems, Inc., Minneapolis, Minn.). The Lytic Enzyme Reagent includes an enzyme to digest cell walls, a buffer, an acid to adjust the pH of the reagent and two stabilizing agents. The digested cells may be used for liquid or solid phase purification described above.

As another aspect of this invention, a kit is provided that includes specific protocols, which in combination with the reagents and optionally the solid supports described herein, may be used for purifying DNA from biological materials according to the methods of the invention. The kit includes instruction means. Depending on the application, the kit may also include any combination of a DNA purifying reagent, DNA Eluting Reagent, RBC Lysis Reagent, Cell Suspension Reagent, Lytic Enzyme Reagent, Protein Digesting Reagent, Isotonic Solution, solid supports, solid supports treated with Lysing Reagent and/or RNA digesting enzyme, vessels to contain the solid supports, vessels to contain the waste liquids, and vessels to contain any eluted DNA. Two preferred DNA Purification Kits are described below.

A kit for purifying DNA using solid phase purification contains: a DNA purifying reagent (e.g., GENERATION® DNA Purification Solution, Gentra Systems, Inc., Minneapolis, Minn.), instruction means, a Lysing Matrix, and a vessel to hold the Lysing Matrix. In this kit the purified DNA remains bound to the solid support for subsequent analysis. Methods to illustrate the use of this kit are given in Examples 5 and 28.

A kit for purifying DNA using solid phase purification and subsequent elution contains: a DNA purifying reagent, instruction means, the DNA Eluting Reagent, a solid support or a Lysing Matrix, a vessel to hold the solid support or the Lysing Matrix, one or more vessels to collect the waste, and a vessel to collect the purified DNA. Methods to illustrate the use of this kit are given in Examples 4, 5, 7, 8, 9, 10, and 25.

In order that the invention may be better understood, specific embodiments for vessels that contain the solid support will now be described in more detail.

In one preferred embodiment of this invention, the vessel is a cartridge equipped with two inlet ports at the top. The inlet ports are attached to vessels upstream containing the sample or reagents through a connector, such as a female Luer-Lock™. One inlet, the sample port, is used for the application of the biological sample to the solid support. An optional feature on the sample port is a self-sealing mechanism that seals the sample port after sample has been transferred through it. The second inlet serves as a reagent port. An optional feature on both inlet ports is a protective breakaway seal. Furthermore, the inlet ports, breakaway seals and diffuser may be housed in an optional screw-cap. At the bottom of the solid support is an optional diffuser with a pore size suitable for the passage of cellular debris, proteins and lipid molecules. The diffuser allows for a uniform traversal of biological material across the cross section of the cartridge, and prevents unequal buildup of biological material anywhere below the solid support. The outlet of the cartridge comes equipped with a protective cap that fits neatly over the tapered barrel. The purified DNA is collected in a collection tube that consists of a conical tube with a snap cap for easy and contamination-free storage. The entire vessel can be scaled in size depending on the size of the samples to be processed and the yields needed for subsequent analysis.

In another preferred embodiment of this invention, the vessel consists of a spin tube designed to hold an insert into which the solid support is packed. The solid support may be cellulose, cellulose acetate, glass fiber, nitrocellulose, nylon, polyester, polyethersulfone, polyolefin, polyvinylidene fluoride, and combinations thereof. The insert consists of a flanged top to hold it in the spin tube and a perforated bottom to allow fluids to pass through while supporting the solid support. A cap tethered to the spin tube was used to cover the insert. Examples of a commercially available spin tube are given in Examples 2, 4, 7, 8, 9, and 10. The biological material passes through the perforated bottom and is collected at the bottom of the spin tube. When used, the biological material is applied to the solid support. The requisite volume of reagent, whether a nucleic acid purifying reagent or eluting reagent, is then added to the solid support. The spin tube is then placed in a centrifuge and subjected to centrifugal forces that draw out the biological material, the purifying reagent and the purified DNA through the solid support during the purification process.

In yet another embodiment, the vessel may be multiple well plates, for example, 6, 12, 24, 48 or 96 well plates where a solid support is packed into each well. The bottom of each well has an exit port through which waste and debris can pass.

This invention will be further described by reference to the following detailed examples. These examples are offered to further illustrate the various specific and illustrative embodiments and techniques. It should be understood, however, that many variations and modifications may be made while remaining within the scope of the present invention.

All of the raw materials mentioned below are readily available from commercial sources such as Sigma Chemical Company, St. Louis, Mo. All percentages are in volume per volume, based on the total volume of the reagent, unless specified otherwise.

EXAMPLES

Example 1

Evaluation of Solid Supports for DNA Purification

Several solid supports, which were cut into small pieces with surface area of about 3 mm diameter or 2 mm square, were evaluated as substrates for DNA purification. A 1 µl volume of whole blood was pipetted onto each solid support, held in a 0.6 ml tube or the well of a 96-well plate, and allowed to dry. To purify the DNA, 200 µl DNA purifying reagent (GENERATION® DNA Purification Solution, Gentra Systems, Inc., Minneapolis, Minn.) were added and incubated for 15 minutes. After pipetting up and down three times to mix, the DNA purifying reagent (containing eluted impurities) was discarded. This washing procedure was repeated twice more for a total of three washes. During this three-step washing procedure, impurities were selectively removed leaving the purified DNA bound to the solid support. Although the solid supports could be dried by evaporation at room temperature to about 80° C., an optional alcohol washing step was used to accelerate the drying process. A volume of 200 µl 100% ethanol was pipetted onto each solid support, incubated for 1 minute and then removed. Isopropanol (2-propanol) at 100% was also found to be a suitable alcohol to accelerate drying.

The ethanol rinse was repeated once more for a total of two rinses and then the disks were allowed to dry at room temperature for at least two hours.

To evaluate the solid supports in a DNA amplification assay, each was transferred to a 0.6 ml tube. Each amplification reaction contained 1× amplification buffer (Promega, Madison, Wis.), 1.5 mM MgCl$_2$, 200 μM each deoxynucleotide, 2.5 units Taq DNA Polymerase (Promega, Madison, Wis.), and primers each at 1 μM specific to the D1S80 locus. The primers were shortened from those given by Budowle et al., *Am. J. Hum. Genet.*, 48, 137-144 (1991) with the oligonucleotide sequences as follows: sense 5' GAA-ACT-GGC-CTC-CAA-ACA-CTG-CCC 3' (SEQ ID NO:1) and antisense 5' GTC-TTG-TTG-GAG-ATG-CAC-GTG-CCC 3' (SEQ ID NO:2). The samples were amplified using 35 cycles of 94° C. for 1 minute, 70° C. for 1 minute, and 72° C. for 2 minutes.

The results showed the presence of D1S80 amplification products using several solid supports. The solid supports that were found to be suitable for DNA purification are listed below. The best results (i.e., the greatest amount of amplification product) were observed using the cellulose paper solid supports.

| Brand Name | Substrate Type | Manufacturer |
| --- | --- | --- |
| S&S 903 ® | cellulose paper | Schleicher and Schuell, Keene, NH |
| Ahlstrom 238 | cellulose paper | Ahlstrom, Mt. Holly Springs, PA |
| BCF180 ® | cellulose paper | Whatman International Ltd. Springfield Mill, England |
| 3MM ® | cellulose paper | Whatman International Ltd. Springfield Mill, England |
| Durapore ® | polyvinylidene fluoride | Millipore Corporation, Bedford, MA |
| BiodyneA ® | charged nylon | Pall Corporation, Port Washington, NY |
| NC/Bind ® | nitrocellulose | Poretics Corporation, Livermore, CA |
| UnifloPlus ® | glass fiber | Schleicher and Schuell, Keene, NH |
| UnifloPlus ® | cellulose acetate | Schleicher and Schuell, Keene, NH |
| Pur-Wrap ® | Dacron ® swab | Hardwood Products, Guilford, ME |
| BiodynePlus ® | charged nylon | Pall Corporation, Port Washington, NY |
| PES Filter | polyethersulfone | Poretics Corporation, Livermore, CA |
| Filtrona ® | polyolefin | American Filtrona, Richmond, VA |
| Leukosorb ® | polyester | Pall Corporation, Port Washington, NY |

Example 2

Rapid Solid Phase Purification of DNA from Whole Blood

To evaluate a rapid solid phase purification method, two blood samples were collected from each of three individuals, one was used fresh and the other was stored frozen at −80° C. for 3 months and then thawed before use. A volume of 3 μl whole blood was pipetted onto a 3 mm diameter disk of S&S 903 paper, which was contained in the insert of a 2 ml spin tube (Spin-X, Catalog No. 9424, Corning Costar, Cambridge, Mass.). A volume of 200 μl nucleic acid DNA purifying reagent (GENERATION® DNA Purification Reagent, Gentra Systems, Inc., Minneapolis, Minn.) was pipetted into the insert and the sample incubated for 1 minute. The DNA purifying reagent was removed by centrifugation at 15,000×g for 10 seconds to collect the eluted impurities in the spin tube. A second and third wash with a DNA purifying reagent was performed in the same way for a total of three washes. Each disk containing purified DNA was transferred to a 0.6 ml siliconized tube for amplification analysis. The waste collected in the spin tube was discarded.

To evaluate the purified DNA samples in an amplification assay, 50 μl PCR amplification solution was added to each disk. Each amplification reaction contained 1× amplification buffer (Promega, Madison, Wis.), 1.5 mM MgCl$_2$, 200 μM each deoxynucleotide, 2.5 units Taq DNA Polymerase (Promega, Madison, Wis.), and 1 μM each primer. Oligonucleotide primers given by Ridker et al., *New Engl. J. Med.*, 332, 912-917 (1995) were used to amplify a factor V gene sequence during 35 cycles, where a cycle was defined as 94° C. for 1 minute, 58° C. for 1 minute, and 72° C. for 1 minute. A 10 μl aliquot from each DNA sample was electrophoresed through a 2% agarose gel at 80 volts for 45 minutes to determine amplification results. The gel and running buffer contained 0.125 μg per ml ethidium bromide to allow visualization of the amplified DNA on a transilluminator.

A factor V amplification product of 223 base pairs was observed for each of the six samples following gel electrophoresis. The amplification results showed that the rapid solid phase DNA purification method, which was performed in about 5 minutes, gave substantially pure DNA from fresh or frozen whole blood.

Example 3

Solid Phase Purification of DNA from Several Biological Samples

At least two DNA samples were prepared from the following biological materials (human source except where noted): whole blood, bone marrow, saliva, buccal cells, cultured K562 lymphoblast cells, *Drosophila melanogaster* (*D. melanogaster*) fruit flies, alfalfa leaves and *Escherichia coli* (*E. coli*) bacteria. Samples of whole blood, bone marrow, saliva and buccal cell scrapes were applied to S&S 903 paper, dried and then sampled by punching a 3 mm diameter disk with a hole punch. Samples of plant or animal tissues were prepared by pressing adult *D. melanogaster* flies or alfalfa first leaves (cotyledons) onto S&S 903 paper. The samples were placed between the collection paper and a piece of PARAFILM "M" (American National Can, Greenwich, Conn.) and pressed with thumb pressure. Cultured cell suspensions were prepared in standard growth medium suitable for either K562 human cells or *E. coli* bacterial cells. A volume of 1 μl medium containing around 10,000 K562 cells or a volume of 5 µl containing around 3 million *E. coli* cells was pipetted onto a 3 mm diameter disk and dried. Then each disk was purified as described in Example 1.

To evaluate the purified DNA samples in an amplification assay, a 50 µl volume of PCR amplification solution was added directly to each tube containing a disk with bound DNA. The PCR solution was as described in Example 2 above except for the primers, which are given below. Whole blood, bone marrow, saliva, buccal cells, *D. melanogaster* tissue, and K562 cells were amplified using primers specific to glyceraldehyde 3-phosphate dehydrogenase (GAPDH) gene sequences given in the mRNA Capture Kit (United States Biochemical Corporation, Cleveland, Ohio). The amplification program used to amplify GAPDH was 30 cycles of 94° C. for 1 minute, 55° C. for 1 minute, and 72° C. for 1 minute. DNA samples from whole blood were also tested for the presence of extrachromosomal DNA by using the mitochondrial primers MT-1 and MT-2 described by Wang et al., *BioTechniques* 17, 76-82 (1994) and the amplification program described above for GAPDH. Alfalfa and *E. coli* DNA samples were tested by using primers specific for 16s-like ribosomal DNA described by Schmidt et al., *BioTechniques*, 11, 176-177 (1991). The amplification program was 30 cycles of 94° C. for 1 minute, 50° C. for 1 minute and 72° C. for 2 minutes. After amplification, 10 µl of the 50 µl reaction were analyzed by agarose gel electrophoresis as described in Example 2.

The results showed that each sample gave the expected amplification product indicating the presence of substantially pure DNA. Amplification of DNA purified from whole blood, bone marrow, saliva, buccal cells, *D. melanogaster* and K562 cells gave an amplification product of about 300 base pairs for GAPDH. Also amplification of DNA purified from whole blood gave an amplification product of about 394 base pairs using primers specific for mitochondrial DNA; this showed that extrachromosal DNA was retained on the solid support disk. From alfalfa and *E. coli* DNA, an amplification product of about 400 base pairs was observed, derived from 16s-like ribosomal DNA amplification.

Example 4

Solid Phase Purification and Elution of DNA from Whole Blood and Buccal Swab Samples To test both wet and dry samples of whole blood and buccal swabs, three samples of each type were collected from three individuals, giving a total of 12 samples. For liquid whole blood samples, a volume of 25 µl was pipetted onto an 8 mm diameter disk of S&S 903 collection paper that had been placed into the insert of a 2 ml spin tube (Spin-X, Catalog No. 9424, Corning Costar, Cambridge, Mass.). For dry whole blood samples, an 8 mm disk was punched from a 300 µl dried blood spot and inserted into the insert of a 2 ml spin tube. Buccal swabs were obtained by swabbing the inner cheek surface 20 times with a sterile cotton-tipped swab (Pur-Wraps®, Hardwood Products, Gilford, Me.). The cotton end of the swab was cut off and placed into the insert of a 2 ml spin tube within two hours of collection for the wet samples and after drying 24 hours for the dry samples. To purify the samples, 200 µl DNA purifying reagent (GENERATION® DNA Purification Solution, Gentra Systems, Inc., Minneapolis, Minn.) were pipetted into each insert and incubated 1 minute for wet samples and 15 minutes for dry samples. The DNA purifying reagent was removed by centrifugation at 15,000×g for 10 seconds to collect the eluted impurities in the 2 ml spin tube. A second and third wash with DNA purifying reagent was performed in the same way for a total of three washes. To elute the purified DNA bound to the solid support, each insert was transferred to a clean 2 ml receiver tube. Then 100 µl DNA Eluting Reagent were pipetted into the insert containing the solid support and heated for 15 minutes at 80° C. in a dry block heater (e.g., VWR Scientific Products Catalog No. 13259-007) fitted with an aluminium block containing 12 mm diameter wells. The DNA Eluting Reagent contained 10 mM Tris, 1 mM NaOH and 0.1 mM EDTA, pH 10.9. After heating, each sample was centrifuged for 20 seconds at 15,000×g to collect the purified DNA.

To evaluate the purified DNA samples in an amplification assay, a 5 µl aliquot was tested from each sample. The amplification procedure described in Example 2 was used.

A factor V amplification product of about 223 base pairs was observed for each of the 12 samples. The results showed that the solid phase purification method gave substantially pure DNA from both wet and dry blood and buccal cell samples using cellulose collection paper and cotton swabs for the solid supports.

Example 5

Purification of DNA in Whole Blood and Cultured Cells Using a Cartridge

A cartridge was constructed using a standard 1 ml polypropylene syringe (Catalog Number 309602, Beckton Dickinson, Franklin Lakes, N.J.) into which was inserted a solid support. The solid support was comprised of cellulose acetate (Filtrona®, American Filtrona, Richmond, Va.) of dimensions about 5 mm diameter×27 mm long. The solid support had been treated previously with 500 µl Lysing Reagent and RNase A and allowed to dry at room temperature for 24 hours. The Lysing Reagent contained 0.5% SDS, 0.1 M Tris, 0.1 M EDTA to which was added 0.04 mg/ml RNase A (about 100 units RNase A per mg). Two whole blood samples and two K562 cultured cells samples each containing about 2 million cells in a 300 µl volume were each pipetted into a cartridge supported in a vertical position. After incubating for 15 minutes at room temperature to allow the cells to lyse and the RNase to digest RNA present in the samples, a 300 µl volume of DNA purifying reagent (GENERATION® DNA Purification Solution, Gentra Systems, Inc., Minneapolis, Minn.) was introduced via 2.5 mm i.d. silicon tubing using a 60 rpm peristaltic pump (Catalog No. MC13003, Markson Science, Hillsboro, Oreg.). After a 1 minute incubation, air was pumped through the cartridge to expel the cartridge contents into a waste container. Then, a second 300 µl volume of DNA purification reagent was pumped into the cartridge and incubated 1 minute. This washing step was repeated once more for a total of three washes with DNA purifying reagent. The solid support in the cartridge was rinsed by pumping 300 µl of DNA Eluting Reagent through it. To remove the purified DNA from the solid support, 300 µl of DNA Eluting Reagent was pumped into the cartridge. The cartridge was plugged at both ends and incubated at 60° C. for 30 minutes in a gravity convection oven. Alternately, an appropriate microwave oven may be used. The cartridge may be heated for 25 minutes at 30% power in a 1100 W Sharp microwave oven. Then the DNA Eluting Reagent, which contained the purified DNA, was pumped out of the cartridge and into a 1.5 ml microcentrifuge tube. Alternately, the DNA eluting reagent can be heated to a temperature greater than 60° C. and then pumped onto the cartridge.

To evaluate the purified DNA samples in an amplification assay, a 5 µl aliquot was tested from each sample. The amplification procedure described in Example 2 was used.

A factor V amplification product of about 223 base pairs was observed for each of the 4 samples. The results showed that the solid phase purification method in a cartridge format gave substantially pure DNA from both whole blood or cultured cell samples.

Example 6

Purification and Restriction Enzyme Digestion of DNA Bound to a Solid Support To further test the quality of DNA purified using a DNA purifying reagent (GENERATION® DNA Purification Solution, Gentra Systems, Inc., Minneapolis, Minn.) while bound to a solid support, seven restriction enzymes were used to test their ability to digest the purified DNA. A volume of 300 µl whole blood from a single individual was pipetted onto S&S 903 paper and dried at room temperature. Then seven 5 mm diameter disks were punched out and each placed into a 0.6 ml tube. A volume of 200 µl DNA purifying reagent was added to each tube and incubated for 15 minutes. After pipetting up and down three times to mix, the DNA purifying reagent was discarded. This washing procedure was repeated twice for a total of three washes. During this three-step washing procedure, impurities were selectively removed leaving the purified DNA bound to the disk. A volume of 200 µl 100% isopropanol (2-propanol) was pipetted onto each disk, incubated for 1 minute and then removed. This was repeated once for a total of two alcohol rinses. The disks containing the purified DNA were allowed to dry at room temperature for two hours.

To test the quality of the DNA bound to each disk, a 25 µl volume of restriction enzyme solution was added directly to each tube. Each restriction enzyme solution contained the appropriate buffer supplied by the manufacturer (New England Biolabs, Beverly, Mass.) and 2.5 mM spermidine (Sigma Chemical Company). The following enzymes were tested with the units added to each reaction specified: Pst I (12 units), Hind III (20 units), Eco RI (20 units), Msp I (20 units), Bam HI (20 units), Hpa I (5 units), and Hae III (10 units). The samples were digested at 37° C. for 4 hours during which time the digested DNA fragments were released from the solid support into the digestion solution. To collect the restriction fragments, each sample tube was pierced with a 27 gauge needle and placed into a clean 0.6 ml tube. The digestion solution was collected by centrifuging at 2,000×g for 2 minutes. To determine whether the purified DNA was digested, a 20 µl volume was removed from each sample and electrophoresed through a 1% agarose gel for 12 hours at 22 volts.

The results showed the presence of a characteristic smear of DNA restriction fragments, ranging from high to low molecular weight for each of the seven enzymes tested. This demonstrated that the DNA samples were substantially pure and suitable for restriction enzyme digestion.

Example 7

Evaluation of Detergents on Solid Support Treatment

Different detergents were tested to determine the best type of detergent needed to optimize DNA yields. The following types of detergents were tested:

| | |
|---|---|
| ANIONIC | Sodium Dodecyl Sulfate (SDS) |
| | Sarkosyl |
| CATIONIC | Dodecyltrimethylam-monium bromide |
| NONIONIC | Tween-20 |
| | Triton X-100 |

Controls were set up with no detergent and with no added sample.

Each of the polysulfone solid supports used had a circumference of 25.31 mm and a height of 9.73 mm (Filtrona®, Lot # 18475, American Filtrona, Richmond, Va.). A volume of 360 µl of a 1% detergent solution was applied to each solid support to saturate it at room temperature for at least 16 hours. Duplicate solid supports were prepared for each treatment. The solid supports were placed into the insert of a 2 ml spin tube (Spin-X, Catalog No. 9424, Corning Costar, Cambridge, Mass.). A whole blood sample containing about 2 million cells in 300 µl was applied to each solid support and allowed to incubate for at least 1 minute at room temperature to allow the cells to lyse. A 200 µl volume of DNA purifying reagent (GENERATION® DNA Purification Solution, Gentra Systems, Inc., Minneapolis, Minn.) was then added. After a 1 minute incubation, the DNA purifying reagent was removed by centrifugation at 15,000×g for 10 seconds to collect impurities in the 2 ml collection tube. This was repeated twice for a total of 3 washes. The waste solution was removed from the receiving tube in between the second and the third wash. The solid support was then rinsed by adding 200 µl of DNA Eluting Reagent (1 mM Tris, 0.001 mM EDTA, 5 mM NaOH) and centrifuging at 15,000×g for 10 seconds. To remove the purified DNA from the support, the insert containing the solid support was transferred to a clean receiver tube and 200 µl of DNA Eluting Reagent was added to it. The solid support was then incubated at 80° C. for 10 minutes in a dry block heater (e.g., VWR Scientific Products Catalog No. 13259-007) and the DNA Eluting Reagent which contained the purified DNA, was removed by centrifugation at 15,000×g for 20 seconds.

Genomic DNA yields and PCR amplification yields were measured to evaluate the purified DNA. To determine relative genomic DNA yields, a volume of 10 µl purified DNA was mixed with 1 µl 10× standard tracking dye and loaded into a 0.7% agarose gel containing 0.125 µg/ml ethidium bromide in the gel and running buffer. The DNA was electrophoresed for 15 minutes at 80 volts and the bands examined visually for band intensity on a UV transilluminator.

The PCR amplification assays was conducted by adding 2.5 µl purified DNA sample directly to a 22.5 PCR amplification mix for a total amplification volume of 25 µl. Each amplification reaction contained 1× amplification buffer (Promega, Madison, Wis.), 1.5 mM $MgCl_2$, 200 µM each deoxynucleotide, 1.25 units Taq DNA Polymerase (Promega, Madison, Wis.), and 1 µM each primer. Primers were sequences specific to the human betaglobin gene: sense 5' CCT-GGC-TCA-CCT-GGA-CAA-CCT-CAA 3' (SEQ ID NO:3) and antisense 5'TAG-CCA-CAC-CAG-CCA-CCA-CTT-TCT 3' (SEQ ID NO:4). The samples were amplified using 35 cycles of 94° C. for 1 minute, 70° C. for 1 minute, and 72° C. for 2 minutes. Then 10 µl of the amplified DNA were loaded into a 2% agarose gel containing 0.125 µg/ml ethidium bromide in the gel and running buffer. The samples were electrophoresed at 80 volts for 45 minutes and the 1.1 kb DNA bands were visualized on a UV transilluminator. The detergents were evaluated by visual ranking of the band intensity for both genomic and amplified DNA as shown in Table 2.

TABLE 2

|  |  | Genomic DNA Yield | PCR Yield |
|---|---|---|---|
| Anionic | Sodium Dodecyl Sulfate (SDS) | 4 | 3 |
|  | Sarkosyl | 3 | 2 |
| Cationic | Dodecyltrimethylammonium bromide | 2 | 1 |
| Nonionic | Tween-20 | 1 | 1 |
|  | Triton X-100 | 1 | 1 |
| No Detergent |  | 1 | 1 |
| No Blood |  | 0 | 0 |

Non-ionic detergents showed no substantial improvement in DNA yield over the controls. The cationic detergent used showed approximately a two fold increase in genomic DNA yield. The two anionic detergents gave the best yield for genomic and amplified DNA.

Example 8

Effects of NaOH concentration, Detergent Type and Solid Support Density on DNA Amplification The effects of NaOH concentration and detergent type, whether anionic or zwitterionic, were examined with two solid support densities. Four solutions were prepared containing 0 or 5 mM NaOH and 1% sodium dodecyl sulfate or 1% CHAPS. CHAPS is a commercially available zwitterionic detergent. A volume of 360 µl of each of these solutions was added to the solid supports as described in Example 7. The two polyolefin solid support densities examined were 0.113 grams fibers/cc (low density) and 0.184 grams fibers/cc (high density) (Filtrona®, American Filtrona, Richmond, Va.). A 300 µl whole blood sample was added to each solid support, washed and eluted as described in Example 7, except using a 150 µl volume of DNA purifying reagent (GENERATION® DNA Purification Solution, Gentra Systems, Inc., Minneapolis, Minn.). The purified DNA was analyzed by PCR amplification and UV spectrophotometry. The PCR protocol used was identical to that described in Example 7. Genomic DNA yields were examined by UV spectrophotometry and by 0.7% agarose gel electrophoresis. To quantitate DNA by UV spectrophotometry, 50 µl of purified DNA was first added to 950 µl deionized water. The UV absorbance was then measured at wavelengths of 320 (background) nm, 260 nm and 280 nm. The yield was calculated as $A_{260} \times 50 \times$ dilution factor×elution volume.

The results showed that there was no detectable difference in DNA yields for solid support treatments carried out using no NaOH and 5 mM NaOH. There was a 2.8 fold increase in DNA yields using SDS over CHAPS. A 75% increase using the high density solid support over the low density solid support was observed.

Example 9

Effects of Chelating Agents, Salts and Detergents on Solid Support Treatment

To determine the effects of chelating agents, salts and detergents on solid support treatment, the polyolefin solid supports were treated with 8 solutions containing 0.5% or 2.0% sodium dodecyl sulfate, 0 or 50 mM EDTA, and 0 or 100 mM NaCl. A 200 µl whole blood sample was added to each solid support, washed, and eluted as described in Example 7. The purified DNA was collected and the genomic DNA yield examined by UV spectrophotometry as described in Example 8. The relative yields were further visualized by agarose gel electrophoresing the purified DNA samples on a 0.7% agarose gel, as described in Example 7. No differences in DNA yields were observed between 0 and 50 mM NaCl. Similarly, no differences in DNA yields were observed between 0 and 50 mM EDTA. However, there was a 3 fold improvement in the yield when 0.5% SDS was used as compared to 2% SDS.

Example 10

Determination of the Optimal Anionic Detergent Concentration

Optimal anionic detergent concentrations were estimated by treating the polyolefin solid support with solutions of sodium dodecyl sulfate (SDS) ranging from 0.2-1.6%. Solid supports were treated with 8 solutions containing 0.2, 0.4, 0.6, 0.8, 1.0, 1.2, 1.4, 1.6% SDS as described in Example 7. A 200 µl whole blood sample was added to each solid support, washed, and eluted as described in Example 7. The purified DNA was collected, and the genomic DNA yield visualized by agarose gel electrophoreses as described in Example 7.

Visual estimation of the band intensity on the 0.7% agarose gel showed that all concentrations of SDS showed good genomic DNA yields although the two highest yields were observed at SDS concentrations of 1.0 and 1.2%.

Example 11

The Effect of Varying Time and Temperature on DNA Elution

The effect of time and temperature on DNA yield was tested using polyolefin solid supports as described in Example 7. DNA from 200 µl blood samples was purified using two 400 µl washes with DNA purification reagent (GENERATION® DNA Purification Solution, Gentra Systems, Inc., Minneapolis, Minn.) and one wash with DNA Eluting Reagent. After adding another volume of 200 µl DNA Eluting Reagent, the samples were incubated for 10 minutes at four elution temperatures in a dry block heater (e.g., VWR Scientific Products Catalog No. 13259-007). The average of three samples for each of the incubation temperatures is given in Table 3.

TABLE 3

| Temperature (° C.) | DNA Yield (µg) |
|---|---|
| 24 | 0.0 |
| 60 | 0.8 |
| 80 | 1.5 |
| 100 | 6.9 |

An incubation temperature of 100° C. gave the highest DNA yield. Additional tests at 120° C. do not indicate a substantial improvement.

The effect of incubation time at 99° C. during the elution step was examined using a second whole blood sample. The same purification protocol described above was followed except that a different dry block heater (Robbins Scientific, TruTemp™, Sunnyvale, Calif.) was used. Results are shown in Table 4.

TABLE 4

| | Time (minutes) | | | | | | | | | |
|---|---|---|---|---|---|---|---|---|---|---|
| | 1 | 2 | 3 | 4 | 5 | 6 | 7 | 8 | 9 | 10 |
| DNA Yield (µg) | 0 | 0 | 0 | 0.8 | 1.0 | 2.7 | 3.0 | 2.6 | 4.3 | 4.0 |

An incubation time of at least 9 minutes at 99° C. was found to give the optimum DNA yield.

Example 12

Design of Vessels to contain the Solid Support

A cartridge was constructed using a standard 1 ml polypropylene syringe (Catalog Number 309602, Beckton Dickinson, Franklin Lakes, N.J.) into which was inserted a solid support. The solid support was comprised of cellulose acetate (Filtrona®, American Filtrona, Richmond, Va.) of dimensions about 5 mm diameter×27 mm long.

In a second design, the cartridge is equipped with two inlet ports at the top. One inlet, the sample port, is used for the application of the biological sample to the solid support. An optional feature on the sample port is a self-sealing mechanism that seals the sample port off after sample has been transferred through it. The second inlet serves as a reagent port. An optional feature on both inlet ports is a protective breakaway seal. At the bottom of the solid support is an optional diffuser with a pore size suitable for the passage of cellular debris, proteins and lipid molecules. The diffuser allows for an equitable dispersal of biological material across the cross section of the cartridge, and prevents unequal buildup of biological material anywhere below the solid support. The outlet of the cartridge comes equipped with a protective cap. The purified DNA is collected in a collection tube that consists of a 0.5 ml conical tube with a snap cap for easy and contamination free storage.

In another vessel design, a spin tube (Spin-X, Corning Costar No. 9424, Cambridge, Mass.) was used with an insert into which was placed a solid support. The solid support used was a polyolefin plug (American Filtrona, Richmond, Va.) which was placed into the insert. The insert consists of a flanged top to hold it in the spin tube and a perforated bottom to allow fluids to pass through while supporting the solid support. A cap tethered to the spin tube was used to cover the insert. An example of a commercially available spin tube is given in Example 1. The biological material passes through the perforated bottom and is collected at the bottom of the spin tube. When used, the biological material is applied to the solid support. The requisite volume of reagent, whether DNA purifying reagent or DNA Eluting Reagent, is then added to the solid support. The spin tube is then placed in a centrifuge and subjected to centrifugal forces that draw out the biological material, the purifying reagent and the purified DNA through the solid support during the purification process.

Example 13

Testing the use of Polyolefin Solid Supports in a 96-Well Plate System

To test the efficacy of DNA purification in a high throughput system, hydrophilic polyolefin solid supports (R-18495, American Filtrona Company, Richmond, Va.) were inserted into wells in a 96-well plate with a well capacity of 800 µl (Unifilter plate manufactured without a filter by Polyfiltronics, Rockland, Mass.). The solid supports were cylindrical in size and had a circumference of 16.7 mm and a length of 10 mm. The aforementioned 96-well sample processing plate was placed on top of another 96 well plate with a 2 ml well capacity which served as a waste collection plate. A volume of 100 µl whole blood was applied to each solid support and allowed to incubate for 1 minute. The solid supports were then subsequently washed twice by adding a volume of 200 µl DNA purifying reagent (GENERATION® DNA Purification Solution, Gentra Systems, Inc., Minneapolis, Minn.) to the well and incubating for 1 minute. The waste material was subsequently removed by centrifuging for 1 minute at 1500×g in a Jouan C412 centrifuge with an M4 rotor fitted with a microplate carrier (Jouan, Winchester, Va.). The solid supports were then washed with 100 µl DNA Eluting Reagent and centrifuged as above without incubation. To elute the purified DNA from the washed solid supports, the processing plate was transferred to a clean standard polystyrene 96-well plate and a volume of 100 µl of DNA Eluting Reagent was added to each well. The stacked processing plate and sample collection plate were placed into a convection oven (BioOven I, St. John's Associates, Beltsville, Md.) set at 80° C. and incubated for 30 minutes. The DNA was subsequently eluted from the solid support by centrifugation at 1500×g for 1 minute. Eight 10 µl sample eluates were analyzed for the presence of DNA by electrophoreses in a 1% agarose gel for 15 minutes at 80 volts. Each of the eight samples contained DNA as visualized by examination on a UV transilluminator.

Example 14

The Effect of Treating a Solid Support with RNase A

A 300 µL volume of Lysing Reagent (0.5% SDS, 0.1 M Tris base, 0.1 M EDTA disodium salt) was applied to a cellulose acetate solid support (American Filtrona, Richmond, Va.) and allowed to dry at room temperature. A second solid support was treated with Lysing Reagent which also contained 0.04 mg/ml RNase A (at 4 mg/ml from Gentra Systems, Inc., Minneapolis, Minn.) and allowed to dry at room temperature. The solid supports had a diameter of 8 mm and a length of 6.75 mm. The two treated solid supports were then placed into the insert of a spin tube (as described in Example 8), and a volume of 150 µl of E. coli overnight bacterial culture added directly to each solid support. E. coli bacterial cultures contain large amounts of RNA and serve as a useful model to test the efficacy of immobilized RNA Digesting Enzyme. The samples were then incubated at 37° C. for 12 minutes to enable RNA digestion. They were subsequently washed three times with a volume of 150 µl DNA purifying reagent (GENERATION® DNA Purification Reagent, Gentra Systems, Inc., Minneapolis, Minn.). Then 150 µl of Basic Eluting Reagent (10 mM Tris, 0.1 M EDTA and 1 mM NaOH) was added to the solid support for 20 minutes at room temperature. The nucleic acids were eluted by centrifuging for 10 seconds at 15,000×g. A volume of 10 µl was analyzed for the presence of DNA by electrophoreses through a 1% agarose gel for 60 minutes at 80 V. Examination of the gel on a UV transilluminator showed clearly the presence of a prominent low molecular weight smear (approximately 0.1-1.4 kb) corresponding to RNA in the sample purified using the solid support with the solid support treated with Lysing Reagent. In contrast, the sample purified with the Lysing Reagent plus RNase lacked the low molecular weight RNA smear showing that the presence of RNase was effective in removing contaminating RNA.

Example 15

DNA Eluting Reagent Optimization for DNA Amplification

The eluting reagent was optimized so as to offer the best DNA yields from the solid support and produce high PCR yields without interfering with the PCR buffering system. Optimal concentrations of base, either NaOH or KOH, Tris buffer and chelating agent (EDTA) were tested on DNA amplification yields using PCR.

Conditions were tested by adding a 25 µl blood sample to a cellulose solid support contained in a spin tube. The cellulose solid support was subsequently washed 3 times with 200 µl DNA purifying reagent (GENERATION® DNA Purification Solution, Gentra Systems, Inc., Minneapolis, Minn.) and 2 times with DNA Eluting Reagent. The samples were all treated identically except for the concentration of base in the DNA Eluting Reagent. Concentrations of 1-8 mM NaOH in the DNA Eluting Reagent were tested.

A TaqMan 7700 Quantitative PCR system, using a β-actin amplification target was used for DNA amplification, as per the manufacturer's recommendation (Perkin Elmer, Applied Biosystems Division, Foster City, Calif.). To test for amplification inhibition, a dilution series was prepared for each test sample and the starting quantity of DNA computed for each. All test samples were compared to the DNA sample at the highest dilution since inhibitors would also be maximally diluted at the highest dilution. If a diluted DNA test sample gave a similar yield to the DNA sample at maximum dilution, (after adjusting by the dilution factor), then no amplification inhibition in that test sample was assumed.

The best PCR yields were obtained at 5-8 mM NaOH. Similar experiments with KOH showed no differences in PCR yields using NaOH or KOH.

Tris buffer concentrations and concentrations of EDTA were tested to determine which concentrations optimized high PCR yields and low amplification inhibition. It was observed that lowering the concentration of Tris buffer from 1 mM to 0.1 mM, and lowering the concentration of EDTA from 0.1 mM to 0.001 mM significantly reduced amplification inhibition.

Example 16

Optimization of Wash and Elution Procedures

Various combinations of wash and elution procedures were tested to determine which combination provided optimal DNA yields and low % amplification inhibition using a TaqMan 7700 Quantitative PCR Instrumentation. The PCR procedures are as described in Example 4.

A volume of 25 µl of blood was applied to a cellulose solid support contained in a spin tube (Spin-X, Corning Costar No. 9424, Cambridge, Mass.) and allowed to absorb for 5 minutes. Each wash with a DNA purifying reagent (GENERATION® DNA Purification Solution, Gentra Systems, Inc., Minneapolis, Minn.) took 2 minutes. DNA Elution Reagent is applied to the solid support for 20 minutes at 80° C. Various purification and elution procedures were tested including the ones listed below. Each procedure was tested in triplicate.

(1) 3×150 µl NA purifying reagent+1×150 µl DNA Eluting Reagent (2) 4×200 µl NA purifying reagent+1×200 µl DNA Eluting Reagent (3) 3×200 µl NA purifying reagent+2×200 µl DNA Eluting Reagent Results are shown in Table 5.

TABLE 5

|  | Human β-Actin DNA Yield (µg) |
|---|---|
| Procedure (1) | 0.509 |
| Procedure (2) | 1.09 |
| Procedure (3) | 1.09 |

Both Procedures (2) and (3) gave good purity and yields.

Example 17

Optimization of Solid Support Treatments

Cellulose solid supports were treated with Lysing Reagents having different compositions for comparison to the untreated solid support. The first composition was composed of 0.5% SDS, 0.1 M Tris and 0.1 mM EDTA, while the second composition was composed of 1% SDS, 10 mM Tris and 0.1 mM EDTA. Cellulose paper was inserted into a spin tube (Spin-X, Corning Costar No. 9424, Cambridge, Mass.) and treated with the two aforementioned compositions. The treated cellulose papers were then allowed to dry for at least 16 hours at room temperature. Untreated cellulose paper was also used as a comparison to the treated samples. A volume of 25 µl of blood was applied to each cellulose solid support and allowed to incubate for 5 minutes. An optimal purification procedure incorporating 3 washes with a DNA purifying reagent (GENERATION® DNA Purification Solution, Gentra Systems, Inc., Minneapolis, Minn.) and 2 washes with DNA Eluting Reagent was conducted. The DNA was collected and analyzed using TaqMan 7700 Quantitative PCR Instrumentation, where a β-actin amplification target was used for DNA amplification, as per the manufacturer's recommendation (Perkin Elmer, Applied Biosystems Division, Foster City, Calif.).

The treatment with 1% SDS gave the best DNA yields. There were no significant detectable differences in DNA yield and % amplification when the level of SDS was reduced to 0.5% from 1.0%. However, the absence of SDS reduced DNA yields by over 50% and increased inhibition from 10% to over 40%.

Example 18

Analysis of DNA Purification: Measurement of DNA Purity

A sample of whole blood was drawn into a vacutainer tube containing EDTA (B-D16852, Becton Dickinson & Co., Franklin Lakes, N.J.) and mixed well. A small aliquot of whole blood was removed and the total number of white cells counted on a CBC5 Cell Counter (Coulter Electronics, Hialeah, Fla.) according to the manufacturer's instructions. This was determined to be $7.25 \times 10^6$ cells/ml. The remainder of the blood was then frozen at −80° C. in 1 ml aliquots until needed for further purification.

Frozen blood was thawed rapidly in a 37° C. water bath and kept on ice until use. Seven 200 µl samples of blood were aliquoted and added to each of seven 2 ml spin tubes (Spin-X, Catalog No. 9424, Corning Costar, Cambridge, Mass.) containing a lysing matrix housed in an insert, and a waste collection tube. The lysing matrix comprised of a cylindrical polyolefin solid support matrix with a diameter of 8 mm, and a height of 8 mm (Filtrona®, Catalog No. 18475, American Filtrona, Richmond, Va.). The polyolefin solid support matrix had been previously saturated with a solution containing 1% SDS and 20 µg/ml RNase A and was subsequently dried.

After the samples were allowed to absorb to the matrix for at least 1 minute, 400 µl DNA purifying reagent (GENERATION® DNA Purification Solution, Gentra Systems, Inc., Minneapolis, Minn.) were added to the sample and allowed to incubate for 1 minute at room temperature. Impurities were collected in the 2 ml spin tube by centrifuging the spin tube at 12,000×g for 10 minutes. The insert containing the solid support was transferred to a second spin tube and the first spin tube was discarded. Another 400 µl DNA purifying reagent was added to the solid support, incubated for 1 minute at room temperature, and the spin tube centrifuged at 12,000×g for 10 minutes. A 200 µl volume of DNA Eluting Reagent was added to the solid support and centrifuged without incubation. Each solid support containing the purified DNA was then transferred to a clean 2 ml spin tube and 200 µl DNA Eluting Reagent added. The tubes were incubated for 10 minutes at 99° C., and the purified DNA was eluted from the solid support by centrifuging at 12,000×g for 20 seconds.

Impurities such as heme are a major contaminant in DNA purification processes involving blood. The presence of heme can be determined using an automated EL311 Microplate Reader (Bio-Tek Instruments, Inc., Winooski, Vt.). Samples were diluted 1:50 in deionized water and a 200 µl volume placed in a 96-well plate. The absorbance was measured at 405 nm. If the absorbance at 405 nm is less than 0.01 nm, the purity of the sample is established. The average visible absorption at 405 nm was 0.004 for the seven samples, indicating a high degree of purity.

Another estimate of DNA purity is the absorbance ratio at 260 nm and 280 nm, $A_{260}/A_{280}$. If the value of this ratio is between 1.7-2.0, the sample is considered relatively free of proteins and other contaminants. This ratio is calculated as follows:

$$(A_{260}-A_{320})/(A_{280}-A_{320})$$

The average $A_{260}/A_{280}$ ratio for the seven samples was found to be 1.95, which indicates substantially pure DNA.

Example 19

Analysis of DNA Purification: Measurement of DNA Concentration and Yield

The seven purified samples from example 18 were further analyzed for concentration and yield. A 1:50 dilution of each sample was prepared in deionized water along with a blank containing DNA Eluting Reagent. Absorbances at 320 nm (background), 260 nm, and 280 nm were read using a Beckman DU64 Spectrophotometer (Beckman Instruments, Inc., Fullerton, Calif.). The DNA concentration was calculated as follows:

$$(A_{260}-A_{320})\times 50(\text{DNA Extinction Coefficient})\times 50 \text{ (Dilution Factor)}$$

The average for the seven samples was found to be 41 µg/ml. This concentration was then multiplied by the volume of the sample (200 µl) to give an average yield of 8.2 µg for each of the seven samples.

The theoretical maximum yield was determined from the white cell count assuming that each human diploid cell has 6 pg DNA. Therefore, based on the following calculation, a theoretical maximum yield of 8.7 µg DNA is obtained.

$$(7.25\times 10^6 \text{ cells/ml})\times(0.2 \text{ ml})\times(6\times 10^{-6} \text{ µg})=8.7 \text{ µg}$$

To calculate the percentage yield, the average yield of 8.2 µg DNA was divided by the theoretical maximum yield of 8.7 µg. This calculation resulted in a percentage yield of 94%.

Following quantitation, the DNA concentration may be adjusted by dilution or concentration as needed. If the DNA is too concentrated, it may be diluted in a diluent such as deionized water. If the DNA is too dilute, it may be concentrated by using a standard alcohol salt precipitation method. In this method, sodium chloride is added to 100 mM with two volumes (relative to DNA sample volume) of 100% ethanol. The sample is mixed by inverting the tube and is centrifuged at 15,000×g for 5 minutes to pellet out the DNA. The DNA pellet is washed by adding 3 volumes of 70% ethanol, inverting the tube and centrifuging at 15,000×g for 1 minute. After discarding the supernatant, the pellet is allowed to air dry for 15 minutes. Then a hydration solution such as deionized water is added to prepare the desired, more concentrated solution.

However, no concentration adjustment of these samples was needed prior to PCR amplification.

Example 20

Analysis of DNA Size

DNA size for each of the seven samples of Example 18 was determined by comparison to the 23.1 kb band of lambda DNA digested with Hind III A volume of 10 µl from each of the seven 200 µl DNA samples was mixed with tracking dye and loaded into a 1% agarose gel. The samples were electrophoresed at 80 volts for 1 hour in 1×TAE running buffer. Both gel and running buffer contained 0.125 µg/ml ethidium bromide so that DNA could be visualized on a transilluminator. Comparison of DNA samples with the marker lanes showed that greater than 95% of the DNA exceeded the 23.1 kb marker indicating that the DNA was of substantially high molecular weight.

Example 21

Testing the Suitability of Purified DNA for PCR Amplification and Subsequent Restriction Enzyme Digestion Each of the seven samples from Example 17 were tested to see if they were suitable for analysis by PCR. A 2.5 µl volume from each of these seven samples was added to a 22.5 PCR amplification mix for a total amplification volume of 25 µl. Each amplification reaction contained 1× amplification buffer (Promega, Madison, Wis.), 1.5 mM Mg Cl$_2$, 200 µM each deoxynucleotide, 1.25 units Taq DNA Polymerase (Promega, Madison, Wis.), and 1 µM each primer. Primers were sequences specific to a region of the HLA-H gene used for hereditary hemochromatosis genetic screening, 5'-TGG-CAA-GGG-TAA-ACA-GAT-CC-3' (SEQ ID NO:5) and 5'-CTC-AGG-CAC-TCC-TCT-CAA-CC-3' (SEQ ID NO:6) (Feder et al., 1995, Nature Genetics 13: 399-408). The samples were amplified using 35 cycles of 94° C. for 1 minute, 58° C. for 1 minute, and 72° C. for 1 minute.

To determine whether the DNA samples were suitable amplification templates, the 7 samples were examined for both the presence and the correct size (388 bp) of an amplification product. A volume of 10 µl from each of the 7 reactions was loaded into a 2% agarose gel containing 0.125 µg/ml ethidium bromide in the gel and running buffer. The samples were electrophoresed at 80 volts for 45 minutes and the DNA bands visualized on a transilluminator. Each of the 7 samples gave a large band of the expected 388 by size showing that the DNA was of a purity suitable for PCR amplification.

The amplified DNA samples were then tested for their ability to be digested by the restriction enzyme Rsa I. This enzyme is used in clinical laboratories to detect a DNA point mutation associated with the genetic disease hereditary hemochromatosis. A 10 µl volume of the amplification reaction was mixed with 5 µl of the Rsa I restriction enzyme mix containing 3.3 mg bovine serum albumin, 3.3 units Rsa I, and 1.5 µl 10× restriction enzyme buffer (all components from New England BioLabs, Beverley, Mass.). The samples were incubated at 37° C. for 30 minutes to allow the restriction enzyme to digest the amplified DNA.

A 15 µl reaction volume of each of the seven samples was electrophoresed in a 2% agarose gel run at 85 volts for 60 minutes. Ethidium bromide was present at 0.125 µg/ml in the gel and running buffer to allow visualization of the bands on a transilluminator. Examination of the gel showed that all seven samples were cut efficiently at the Rsa I restriction site such that the 388 by band was absent. In each of the 7 lanes, two bands were visible of approximately 250 and 140 by in size.

Example 22

Restriction Enzyme Digestion and Southern blotting Analysis of DNA purified using DNA Purifying Reagents DNA from seven 5 mm diameter dried blood spots was purified, digested and electrophoresed as described in Example 6. Following electrophoreses, the restriction fragments were transferred over a 7 hour period to a nylon membrane (Biotrans+™, ICN Biomedicals, Inc., Irvine, Calif.) by Southern blotting using a transfer solution containing 0.4 N NaOH and 0.6 M NaCl. The nylon blot was hybridized for 14 hours at 65° C. in HYB-9® Hybridization Solution (Gentra Systems, Inc., Minneapolis, Minn.) and then washed according to the manufacturer's instructions. The probe was prepared from an amplified 300 by region of the glyceraldehyde 3-phosphate dehydrogenase labeled with $^{32}$P-labeled dCTP using a random priming kit (Amersham Life Science, Inc., Arlington Heights, Ill.). The membrane was placed against X-ray film (XAR5, Eastman Kodak Company, Rochester, N.Y.) between two intensifying screens at −80° C. for 14 hours. The resulting autoradiogram showed bands in each of the lanes corresponding to digested DNA complementary to GAPDH sequences in the genome.

Example 23

Evaluation of Potential Cross-Contamination in DNA Purification Methods

Test materials: Whole blood (Memorial Blood Center of Minneapolis), 8E5 cultured cells (Folk, et al., 1986, Guenthner et al., 1998), or phosphate-buffered saline (PBS) were loaded on lysing matrix contained in two different vessel formats (Capture Plate™, Gentra Systems Inc., Minneapolis, Minn. and Capture Column™, Gentra Systems Inc., Minneapolis, Minn.). The Capture Column™ consists of a lysing matrix enclosed in an insert which is placed in a centrifuge tube. The Capture Plate™ consists of 96 flow-through wells each enclosing a lysing matrix. The bottom of each well has a tapered exit port.

Experimental Set-up: A 200 µl sample volume of blood or PBS was added to the Capture Column™ tubes or Capture Column™ wells using aerosol resistant tips.

Purification Method: Samples were purified by washing twice with 400 µl DNA purifying reagent, (DNA Purification Solution™, Gentra Systems Inc., Minneapolis, Minn.) and 1 wash with 200 µl volume of a DNA eluting reagent (DNA Elution Solution Gentra Systems Inc., Minneapolis, Minn.). Capture Columns™ were centrifuged between washes for 10 seconds at 13,000×g and Capture Plates™ were centrifuged for 3 minutes at 2000×g. Fresh sealing film was applied to each plate between washes to prevent contamination. Sample elution was performed by adding 200 µl DNA Elution Solution™ to each well. Capture Columns™ were heated at 99° C. for 10 minutes in a block heater and Capture Plates™ were heated for 25 minutes at 30% power in a 1100W Sharp microwave oven. Following centrifugation the eluates were ready for amplification.

Amplification: A 2 µl sample of each eluate was amplified to detect contaminating DNA in the samples without DNA (PBS). HLA-H primers (Feder et al., 1996) were used for experiments using blood and HIV-1 (gag) primers (Guenthner et al., 1998) were used for 8E5 cultured cells. The cycling conditions used were: 40 cycles of: 94° C. for 30 seconds, 58° C. for 30 seconds, and 72° C. for 30 seconds in a PE2400 or 9700 thermal cycler.

Detection: For gel analysis of Capture Column™ amplification products, 5 µl of the 25 µl reaction were loaded onto a 2% gel and electrophoresed at 80 volts for 45 minutes. For gel analysis of Capture Plate™ amplification products, a 96-well format minigel (2% agarose) was used at 80 volts for 5 minutes. For TaqMan detection on a PE7200 Sequence Detection System, fluorescent probes for HLA-H and HIV were synthesized by PE Applied Biosystems.

24. Sample Collection and Handling for DNA Purification on a Solid Support

DNA is purified from whole blood, bone marrow, buffy coat, body fluids, cultured cells and solid tissue on a lysing matrix (Capture Column™, Gentra Systems Inc., Minneapolis, Minn.). Prior to purification on the Capture Column™, samples were processed as follows:

i. Whole Blood and Bone Marrow

Whole blood and bone marrow were collected in EDTA to reduce DNA degradation. However, other anticoagulants such as ACD (citrate) and heparin may be used successfully. Samples may be either fresh or frozen. However, improved yields may be observed using frozen samples. Frozen samples are stable at −80° C. for at least two years. Before use, the samples are thawed quickly in a 37° C. water bath and kept on ice until use. If the blood or bone marrow is not frozen, it is recommended that it be stored at 4° C. A 200 µl volume of blood or bone marrow may be used for DNA purification. If it is necessary to purify DNA from a larger volume, a buffy coat sample may be prepared.

ii. Buffy Coat

Whole blood was collected in EDTA to reduce DNA degradation. However, other anticoagulants such as ACD (citrate) and heparin may be used successfully. The fresh samples were stored at 4° C. White blood cells were isolated rapidly using an adequate lysing reagent (Lysis Solution™, Gentra Systems Inc., Minneapolis, Minn.). Alternatively, buffy coat may be prepared from up to 5 ml whole blood by centrifuging the sample at 800×g for 10 minutes at room temperature. Alternatively, the tube containing blood may be placed in a vertical position at 4° C. overnight to allow cells to settle. A thin layer of white blood cells (buffy coat) should be visible between the upper plasma layer and the lower red blood cell layer. The upper plasma layer is removed and the buffy coat is carefully collected with a pipet, and kept on ice until use. DNA may be purified from up to 200 buffy coat preparation containing a maximum of 10 million white blood cells.

iii. Body Fluids (Examples include saliva, synovial fluid, cerebrospinal fluid, urine, amniotic fluid, plasma and serum.)

Body fluid samples are collected and stored at 4° C. and used as quickly as possible. Alternatively, they may be stored frozen at −80° C. For body fluids with low cell numbers, it is preferable to concentrate samples by centrifugation. Cells from a 3-40 ml volume of body fluid were pelleted by centrifuging at 2,000×g for 10 minutes. The supernatant was removed leaving behind 200 μl to 1 ml residual fluid. The pellet in the residual fluid was thoroughly suspended by pipetting up and down 10 times and kept on ice or stored frozen at −80° C.

iv. Cultured Cells

Fresh samples and those stored frozen at −80° C. were used. The suspended cultured cells were collected and place on ice until use. Cell counts were obtained using a hemacytometer or other cell counter. A 200 μl suspension containing up to 10 million cultured cells was added directly to the Capture Column™.

v. Solid Tissue

Fresh samples and those stored frozen at −80° C. were used. The samples were kept on ice at all times to reduce DNase activity. 20 mg tissue was added to a 1.5 ml microfuge tube containing 30 μl cold PBS[1/] (preferably containing 1 mM EDTA to reduce Dnase activity) and was quickly homogenized with a microfuge tube pestle. The sample was placed on ice to allow cell clumps to settle for 2 to 10 minutes. The upper 200 μl cell suspension was then removed excluding any cell clumps.

[1/] PBS with EDTA: 8 gm NaCl, 0.2 gm KCl, 2.72 gm $Na_2HPO_4.7H_2O$, 0.24 gm $KH_2PO_4$, 0.372 gm EDTA disodium salt dissolved in ultrapure water, brought up to a volume of 1,000 ml and autoclaved.

vi. Gram-negative Bacteria

Fresh samples and those stored frozen at −80° C. were used. The samples were kept on ice. Typically, an overnight culture contains 1-3 billion cells per ml. However, due to the smaller genome size of Gram-negative bacteria, up to 3 billion cells were applied to the column for DNA purification. The culture was centrifuged, washed, resuspended and applied to the column.

Example 25

DNA Purification on a Lysing Matrix

The samples from Example 24 were purified on a lysing matrix (Capture Column™ Gentra Systems, Minneapolis, Minn.) as follows:

i. Sample Purification

1. A volume of 200 μl of a well-mixed sample was added to the Capture Column™ and allowed to absorb at room temperature for at least 1 minute or up to 1 hour.
2. A volume of 400 μl of a DNA purifying reagent (DNA Purification Solution™, Gentra Systems, Minneapolis, Minn.) was added and allowed to incubate for 1 minute at room temperature.
3. The Capture Column™ was centrifuged for 10 seconds at 2,000-12,000×g. A waste volume of 600 μl was collected in the waste collection tube.
4. A volume of 400 μl DNA Purification Solution™ was added again to the Capture Column™ and allowed to incubate for 1 minute at room temperature.
5. The Capture Column™ was then centrifuged for 10 seconds at 2,000-12,000×g and the waste volume was collected.
6. A volume of 200 μl DNA Elution Solution™ was then added. The Capture Column™ was centrifuged as described above.
7. The Capture Column™ was transferred to a DNA collection tube and the waste was discarded.
8. A volume of 200 μl DNA Elution Solution™ was added and allowed to incubate for 10 minutes in a dry block heater pre-heated to 99° C. The Capture Column™ was then centrifuged as previously described to release DNA from the lysing matrix.
9. The purified DNA was then ready for analysis.

ii. DNA Storage

The purified DNA is stable for at least 3 months at 4° C. For long term storage, it can be stored at −20° C.

Example 26

DNA Quantification Using UV Spectrophotometric Analysis

Water is often used for diluting DNA for UV spectrophotometric analysis. However, there can be significant variability in both the $A_{260}/A_{280}$ ratio and the yield determined when water is used as a diluent. Commercial buffers such as Tris-based or phosphate based buffers may be used to overcome these problems. Consistent results are obtained by diluting DNA samples in TE Buffer™ (10 mM Tris, 11 mM EDTA pH 8.0) (Gentra Systems, Minneapolis, Minn.) as described below. Additional consistency is obtained by using a masked quartz cuvette (e.g., Beckman Instruments, Inc. Semi-Microcell Masked Cuvette Cat. No. 533041).

ii. Sample Preparation and UV Spectrophotometric Analysis

1. Purified DNA samples are gently vortexed for 5 seconds.
2. Dilution tubes were prepared by adding 190 μl TE Buffer™ to 0.6 ml microfuge tubes.
3. A blank solution was prepared by diluting a volume of 10 μl DNA Eluting reagent (DNA Elution Solution™, Gentra Systems, Minneapolis, Minn.) with 190 μl TE Buffer™ in a 0.6 ml microfuge tube.

4. 10 µl DNA was removed from each sample and mixed with TE Buffer™ to make a total volume of 200 µl, giving a 1:20 dilution.
5. The diluted samples were then vortexed at high speed for 5 seconds.
6. A volume of 200 µl diluted sample was used to determine yield and purity using a UV spectrophotometer by determining absorbances at 26 nm, 280 nm and 320 nm.

iii. DNA Yield and Purity Calculations
1. To calculate the DNA concentration of each sample: $(A_{260}-A_{320}) \times 50 \times$ dilution factor (e.g., 200/10)=DNA concentration in µg/ml. Note: $A_{320}$ measures background scatter.
2. To calculate the DNA yield: DNA concentration(µg/ml)×volume of Elution Solution (0.2 ml)=DNA yield (µg).
3. To calculate DNA purity: $(A_{260}-A_{320})/(A_{280}-A_{320})$=purity of the DNA. The $A_{260/280}$ ratio should be at least 1.5, however, this ratio may not be an accurate measure of DNA purity (see references 1, 2, 3). This ratio was first used to detect nucleic acid contamination in protein preparations and as such, is a poor indicator of DNA quality. DNA quality can be better assessed by simply analyzing the DNA by agarose gel electrophoresis or by evaluating performance (e.g., by PCR amplification).

27. DNA Purification on a Flat Solid Support

Fresh or frozen biological samples were collected and processed as described in Example 24. Large sample volumes (e.g. 300 µl) were pipetted onto a flat solid support (Collection Cards™, Gentra Systems, Minneapolis, Minn.), dried and then sampled by punching out a disk prior to DNA purification. Samples may be stored on the Collection Cards at room temperature for at least 9 months or at −20° C. for long term storage.

The following samples were collected and allowed to dry on the Collection Card in a horizontal position at room temperature for two hours.

i. Whole Blood (obtained via skin puncture or venipuncture)

ii. Buccal Cells (epithelial cells from inner cheek)

iii. Body Fluids (saliva, urine, plasma, serum)

iv. Cultured Cells

DNA Purification

The sample was removed from the Collection Card by punching a 3 mm disk with a clean hole punch, and then purified in a 96-well plate, a 0.2 ml or 0.6 ml microfuge tube. The 3 mm disk was placed in a well of a 96-well plate and the plate was positioned in a robotic workstation. (Alternatively, the samples may be processed manually in a 96-well plate using a multichannel pipet or in a 0.2 or 0.6 ml tube using a micropipet). A volume of 200 µl of DNA purifying reagent (DNA Purification Solution, Gentra Systems, Minneapolis, Minn.) was added and allowed to incubate for 15 minutes at room temperature causing the DNA to remain bound to the disk while the contaminants were released. The solution was mixed by pipetting and then removed. This process was repeated twice. A volume of 200 µl 100% isopropanol or 100% ethanol was then added and allowed to incubate for 1 minute at room temperature. The alcohol was removed, and the alcohol wash repeated. The disk was then dried at room temperature for at least 1-16 hours to evaporate the alcohol. After drying, the sample disks were light orange to white in color. The purified disks are stable for at least 9 months at room temperature or at −20° C. for long term storage.

DNA Amplification
1. If the disk was purified in a 0.2 or 0.6 ml amplification tube, at least 50 µl amplification solution was added directly to the tube. If the disk was purified in a 96-well flat bottom plate, the purified DNA sample disk was transferred to an amplification tube at least 50 µl amplification solution was then added. The disk was completely submerged in the amplification solution. The sample was then amplified using standard conditions.
2. The disk may be stored in amplification solution for at least 4 months at room temperature.

Re-Use for DNA Sample Disks

The purified DNA disks may be washed and re-used at least 5 times.
1. The disk is removed from the amplification tube and subsequently transferred to a filter insert contained within a 2 ml receiver centrifuge tube.
2. 200 µl DNA purifying reagent (DNA Purification Solution, Gentra Systems, Minneapolis, Minn.) is pipetted into the filter insert and centrifuged at 13,000-16,000×g for 5 seconds to wash the disk. This wash is repeated once more for a total of 2 washes.
3. The wash solution in the receiver tube is discarded and the washed disk is transferred to a new amplification tube. The amplification solution is added and amplified as described above.

Example 28

Purification of DNA from Biological Samples on a Lysing Matrix Disk and Subsequent Amplification DNA was purified from five biological samples on lysing matrix disks (Capture Disk, Gentra Systems, Minneapolis, Minn.). The quality of the DNA was ascertained using PCR amplification.

Biological samples were collected and prepared as follows: human whole blood and bone marrow were collected in tubes containing EDTA (Becton Dickinson No. 6457); a buffy coat was isolated from 0.2 ml whole blood collected in EDTA; a 0.5 ml urine sediment was prepared by centrifuging a 40 ml urine sample at 800×g for 10 minutes; and 1 million K562 cells were suspended in 0.3 ml culture medium. DNA was purified from 3 of each prepared sample as described in the following sections. Each 3 mm disk containing purified DNA was amplified in a 50 µl reaction using primers specific of the HLA-H locus (used for hereditary hemochromatosis screening). A 388 base pair amplification product was expected.

Sample Collection and Handling
i. Buffy Coat Preparation
Whole blood or bone marrow was collected in EDTA to reduce DNA degradation. However, other anticoagulants such as ACD (citrate) and heparin may be used successfully. White blood cells were isolated from the red blood cells in the sample by using an RBC lysis reagent (PUREGENE® RBC Lysis Solution, Gentra Systems, Minneapolis, Minn.). Alternatively, the buffy coat may be prepared by centrifuging the sample at 800×g for 10 minutes at room temperature. A thin layer of white blood cells (buffy coat) should be visible between the upper plasma layer and the lower red blood cell layer. The upper plasma layer was removed and the buffy coat collected with a pipet and kept on ice. A 3 µl suspension of buffy coat containing at least 2,100 white blood cells was then added to the Capture Disk.

ii. Body Fluids

Examples of body fluids include saliva, synovial fluid, cerebrospinal fluid, urine, amniotic fluid, plasma and serum. For body fluids with low cell numbers, samples are concentrated by centrifugation. Cells from a 3-40 ml volume of body fluid are pelleted by centrifuging at 800×g for 10 minutes. The supernatant is removed and the pellet is suspended in the residual fluid and kept on ice.

iii. Cultured Cells

The number of cells was determined using a hemacytometer or other cell counter. A 3 µl suspension containing at least 2,100 cultured cells was added to the lysing matrix disk.

iv. Gram-negative Bacteria

A 3 µl suspension containing at least 600,000 bacterial cells was added to the lysing matrix Disk. Typically, an overnight culture of bacteria contains 1-3 billion cells per ml. Thus, the culture can be used directly, or if necessary, concentrated by centrifugation.

v. Mouse Saliva

A mouse was restrained in a vertical position, and 3-5 µl saliva was removed from underneath the tongue of the mouse using a micropipettor.

vi. Whole Blood or Bone Marrow

Whole blood or bone marrow was collected in EDTA to reduce DNA degradation. However, other anticoagulants such as ACD (citrate) and heparin may be used successfully. A 3 µl volume of blood or bone marrow was used for DNA purification.

DNA Purification

The above samples are purified as follows:
1. A volume of 3 µl well-mixed sample was pipetted onto a 3 mm lysing matrix disk in the insert of a 2 ml spin tube. The sample was allowed to absorb at room temperature for at least 1 minute or up to 2 hours.
2. A volume of 200 of DNA purifying reagent (DNA Purification Solution, Gentra Systems, Minneapolis, Minn.) was added to the insert and allowed to incubate for 1 minute at room temperature.
3. The spin tube was centrifuged at 2,000-16,000×g for 10 seconds to collect the wash solution in the receiver tube.
4. The incubation with the DNA purifying reagent and the centrifugation was repeated twice. The lysing matrix disk containing the immobilized purified DNA was white or off-white in color. The immobilized DNA was then ready for DNA amplification.

DNA Amplification

The disk was placed directly into an amplification tube. A volume of 25-50 amplification master mix was added to the tube, and the DNA was amplified using standard conditions. The disk was stored in the amplification solution for at least 4 months at room temperature.

Sample Re-Use

The disk may be re-used for further amplification. The protocol is as follows: The disk is washed twice with 200 µl of DNA Purification Solution and centrifuged at 2,000-16,000×g for 5 seconds before amplification.

What is claimed is:

1. A kit for isolating DNA comprising:
   (a) optionally instruction means for isolating substantially pure DNA from a biological sample;
   (b) a DNA purifying composition;
   (c) a DNA eluting reagent; and
   (d) a solid support selected from a group consisting of glass fiber, nylon, polyester, polyethersulfone, polyolefin, polyvinylidene fluoride, and combinations thereof,
   wherein the DNA eluting reagent comprises:
   (i) a buffer;
   (ii) a base;
   (iii) a chelating agent; and
   (iv) water,
   wherein the chelating agent is present in an amount no greater than 0.1 mM based on the total volume of the DNA eluting reagent, the base is present in an amount between 5-8 mM, and the combined amount of buffer, base, and chelating agent is present in an amount no greater than 20 mM based on the total volume of the DNA eluting reagent.

2. The kit of claim 1, further comprising a vessel for holding the solid support.

3. The kit of claim 1, wherein the solid support is treated with a lysing reagent.

4. The kit of claim 1, wherein the solid support is treated with an RNA digesting enzyme.

5. The kit of claim 1, further comprising an RBC Lysis Reagent comprising ammonium chloride, sodium bicarbonate, and EDTA, for use in separating white cells from red blood cells in mammalian whole blood prior to DNA isolation.

6. The kit of claim 1, further comprising:
   (a) a cell suspension reagent comprising Tris, EDTA, and sorbitol; and
   (b) a lytic enzyme reagent comprising a lytic enzyme, glycerol, Tris, and calcium chloride, wherein the cell suspension reagent and the lytic enzyme reagent are suitable for use in combination to digest cell walls of yeast and Gram-positive bacteria.

7. The kit of claim 1, further comprising a reagent selected from the group consisting of:
   (a) an RBC Lysis reagent;
   (b) a cell suspension reagent;
   (c) a lytic enzyme reagent;

(d) a protein digesting reagent; and
(e) an isotonic solution.

8. The kit of claim 1, wherein the chelating agent is present in the amount of about 0.0001 to about 0.05 mM.

9. The kit of claim 1, wherein the chelating agent is present in the amount of about 0.0001 to about 0.015 mM.

10. A kit for isolating DNA comprising:
(a) optionally instruction means for isolating substantially pure DNA from a biological sample;
(b) a DNA purifying composition;
(c) a DNA eluting reagent, and
(d) a solid support selected from a group consisting of glass fiber, nylon, polyester, polyethersulfone, polyolefin, polyvinylidene fluoride, and combinations thereof,
wherein the DNA eluting reagent comprises:
(i) a buffer;
(ii) a base;
(iii) a chelating agent; and
(iv) water,
wherein the chelating agent is present in an amount no greater than 0.1 mM based on the total volume of the DNA eluting reagent, the base is present in an amount between 5-8 mM, and the combined amount of buffer, base, and chelating agent is present in an amount no greater than 20 mM based on the total volume of the DNA eluting reagent, and wherein the DNA eluting reagent contains no greater than 50 mM NaCl.

11. A method for isolating DNA using the kit of claim 1, comprising the steps of:
(a) contacting a biological material that contains DNA with the solid support from the kit of claim 1;
(b) treating the biological material that contains DNA with a DNA purifying reagent;
(c) purifying the DNA from the remainder of the biological materials; and
(d) eluting the DNA from the solid support with the DNA eluting reagent from the kit of claim 1.

12. The method of claim 11, wherein the DNA eluting reagent has a pH of at least 7.

13. The method of claim 11, wherein the base is chosen from the group consisting of alkaline metal hydroxides.

14. The method of claim 11, wherein the buffer is present in an amount from 0.001-20 mM based on the total volume of the DNA eluting reagent.

15. The method of claim 11, wherein the buffer is present in an amount from 0.01-15 mM based on the total volume of the DNA eluting reagent.

16. The method of claim 11, wherein the solid support is contained in a vessel, wherein the vessel is selected from a group consisting of centrifuge tubes, spin tubes, syringes, cartridges, chambers, multiple-well plates, test tubes, and combinations thereof.

17. The method of claim 11, wherein the biological material is selected from the group consisting of eukaryotic cells, prokaryotic cells, microbial cells, bacterial cells, plant cells, mycoplasma, protoza, bacteria, fungi, viruses, and lysates and homogenates thereof.

18. The method of claim 11, wherein the biological material is selected from the group consisting of body fluids, body waste products, excretions, and tissues.

19. The method of claim 11, wherein the biological material is selected from the group consisting of environmental samples taken from air, water, sediment and soil.

20. The method of claim 11, wherein the buffer is Tris, the chelating agent is EDTA, and the base is chosen from the group consisting of alkaline metal hydroxides.

21. The method of claim 11, further comprising the step of heating at greater than 60° C.

* * * * *